(12) United States Patent
Birbaum et al.

(10) Patent No.: US 6,703,182 B1
(45) Date of Patent: Mar. 9, 2004

(54) UNSATURATED OXIME DERIVATIVES AND THE USE THEREOF AS LATENT ACIDS

(75) Inventors: Jean-Luc Birbaum, Binningen (CH); Toshikage Asakura, Minoo (JP); Hitoshi Yamato, Hyogo (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/763,016
(22) PCT Filed: Aug. 6, 1999
(86) PCT No.: PCT/EP99/05698
§ 371 (c)(1), (2), (4) Date: Feb. 15, 2001
(87) PCT Pub. No.: WO00/10972
PCT Pub. Date: Mar. 2, 2000

(30) Foreign Application Priority Data

Aug. 19, 1998 (EP) ............................. 98810810

(51) Int. Cl.$^7$ .............................................. G03C 1/492
(52) U.S. Cl. ................... 430/270.1; 430/919; 430/921; 522/59; 564/258; 564/268
(58) Field of Search .............................. 430/270.1, 919, 430/921; 522/59; 564/258, 268

(56) References Cited

U.S. PATENT DOCUMENTS

| | | | | |
|---|---|---|---|---|
| 4,123,255 A | * | 10/1978 | Freenor et al. | 504/312 |
| 4,346,094 A | * | 8/1982 | Beck et al. | 514/372 |
| 4,347,372 A | * | 8/1982 | Fory et al. | 548/217 |
| 4,510,294 A | * | 4/1985 | Taylor | 525/369 |
| 4,540,598 A | * | 9/1985 | Berner et al. | 427/518 |
| 5,019,488 A | * | 5/1991 | Mammato et al. | 430/325 |
| 5,627,011 A | | 5/1997 | Münzel et al. | 430/270.1 |
| 5,714,625 A | | 2/1998 | Hada et al. | 558/437 |
| 5,759,740 A | | 6/1998 | Mënzel et al. | 430/270.1 |
| 5,800,964 A | * | 9/1998 | Sato et al. | 430/281.1 |
| 6,017,675 A | * | 1/2000 | Dietliker et al. | 430/270.1 |
| 2002/0020832 A1 | * | 2/2002 | Oka et al. | 252/500 |

FOREIGN PATENT DOCUMENTS

| | | | |
|---|---|---|---|
| EP | 241423 A2 * | 10/1987 | G03F/7/10 |
| EP | 361907 A2 * | 4/1990 | G03F/7/004 |
| EP | 780729 A1 * | 6/1997 | G03F/7/004 |
| GB | 2306958 | 5/1997 | |
| JP | 09095479 A * | 4/1997 | C07C/309/65 |
| WO | 98/10335 | 3/1998 | |
| WO | WO 9810335 * | 3/1998 | G03F/7/004 |

OTHER PUBLICATIONS

G. Nawwar et al., Heterocycles, vol. 38, No. 1, (1994), pp. 71–80.

* cited by examiner

Primary Examiner—Janet Baxter
Assistant Examiner—Yvette C. Thornton
(74) Attorney, Agent, or Firm—Tyler A. Stevenson

(57) ABSTRACT

Compounds of formulae I, II or III

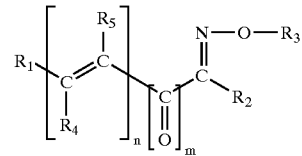
(I),

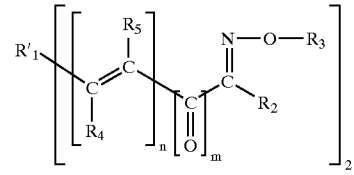
(II)

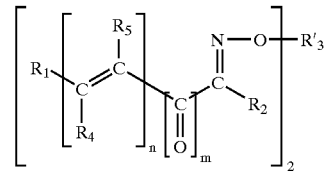

(III), wherein m is zero or 1; n is 1, 2 or 3; $R_1$ inter alia is unsubstituted or substituted phenyl, or naphthyl, anthracyl, phenanthryl, a heteroaryl radical, or $C_2$–$C_{12}$alkenyl; $R'_1$ inter alia is vinylene, phenylene, naphthylene, diphenylene or oxydiphenylene; $R_2$ inter alia is CN, $C_1$–$C_4$haloalkyl, $C_2$–$C_6$alkoxycarbonyl, phenoxycarbonyl, or benzoyl; $R_3$ inter alia is $C_1$–$C_{18}$alkylsulfonyl, phenyl-$C_1$–$C_3$alkylsulfonyl, camphorylsulfonyl, or phenylsulfonyl; $R'_3$ inter alia is $C_2$–$C_{12}$alkylenedisulfonyl, phenylenedisulfonyl, naphthylenedisulfonyl, diphenylenedisulfonyl, or oxydiphenylenedisulfonyl; $R_4$ and $R_5$ inter alia are hydrogen, halogen, $C_1$–$C_8$alkyl, $C_1$–$C_6$alkoxy, $C_1$–$C_4$haloalkyl, CN, $NO_2$, $C_2$–$C_6$alkanoyl, benzoyl, phenyl, —S-phenyl, $OR_6$, $SR_9$, $NR_7R_8$, $C_2$–$C_6$alkoxycarbonyl or phenoxycarbonyl; $R_6$ inter alia is hydrogen, phenyl or $C_1$–$C_{12}$alkyl; $R_7$ and $R_8$ inter alia are hydrogen or $C_1$–$C_{12}$alkyl; $R_9$ inter alia is $C_1$–$C_{12}$ alkyl; $R_{10}$, $R_{11}$ and $R_{12}$ inter alia are $C_1$–$C_6$alkyl or phenyl; upon irradiation react as acid generating compounds and thus are suitable in photoresist applications.

15 Claims, No Drawings

UNSATURATED OXIME DERIVATIVES AND THE USE THEREOF AS LATENT ACIDS

The invention relates to new unsaturated oxime derivatives, photopolymerisable compositions comprising said compounds and to the use of the compounds as latent acids, which can be activated by irradiation with light.

In U.S. Pat. No. 4,540,598 surface-coating compositions based on photosensitive oxime sulfonates and customary acid-curable resins are disclosed. In EP 571330 the use of α-(4-toluene-sulfonyl-oxyimino)-4-methoxybenzyl cyanide and α-(4-toluene-sulfonyloxyimino)-3-thienylmethyl cyanide as latent acid donors in positive and negative photoresists for wavelengths of 340–390 nm, especially those in the radiation region of the mercury i line (365 nm) is described. In GB 2306958 the use of oxime-sulfonates as latent acid donors in positive and negative photoresists for wavelengths between 180 and 600 nm, especially those in the radiation region beyond 390 nm is reported. In U.S. Pat. No. 5,714,625 non aromatic α-(alkylsulfonyloxyimino)-1-cyclohexenylacetonitriles and α-(alkylsulfonyloxyimino)-1-cyclopentenylacetonitriles are disclosed. In Heterocycles, 38, 71 (1994), G. Nawwar et al. disclose 2-(p-tolylsulfonyloxyimino)-3-oxo-5-phenyl-pent-4-enenitrile as experimental product for investigations on a synthesis for pyrano-pyrroles.

In the art, a need still exists, especially for reactive non-ionic latent acid donors that are thermally and chemically stable and that, after being activated by light, can be used as catalysts for a variety of acid-catalysed reactions, such as polycondensation reactions, acid-catalysed depolymerisation reactions, acid-catalysed electrophilic substitution reactions or the acid-catalysed removal of protecting groups. There is also a need for compounds that when irradiated with light are converted into acids and are capable of acting as solubility inhibitors in resist formulations. Furthermore there is a need for photolatent acids which can be bleached upon irradiation.

Surprisingly, it has now been found that specific unsaturated oxime derivatives possessing at least one olefinically unsaturated double bond or triple bond which is conjugated with another olefinically unsaturated double bond or with an aromatic or heterocyclic double bond, are especially suitable as catalysts for such reactions. The optical absorption spectra of the specific compounds of the invention are particularly tunable over a wide range of the electromagnetic spectrum. Furthermore they can be bleached upon irradiation.

Accordingly, the present invention pertains to compounds of the formulae I, II or III

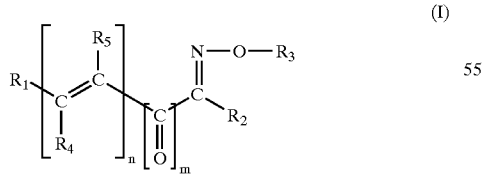
(I)

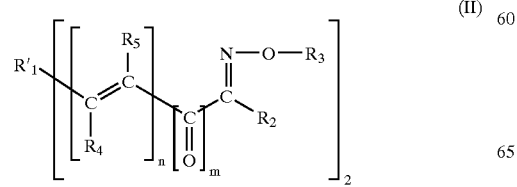
(II)

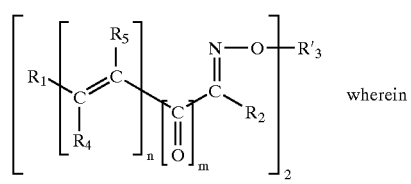
(III), wherein m is zero or 1;

n is 1, 2 or 3;

$R_1$ is phenyl, which is unsubstituted or substituted by one or more of the radicals $C_1$–$C_{12}$alkyl, $C_1$–$C_4$haloalkyl, halogen, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$, with further substituents on the phenyl ring or with one of the carbon atoms of the phenyl ring; or $R_1$ is naphthyl, anthracyl or phenanthryl, wherein the radicals naphthyl, anthracyl and phenanthryl are unsubstituted or substituted by $C_1$–$C_6$alkyl, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$ with further substituents on the naphthyl, anthracyl or phenanthryl ring or with one of the carbon atoms of the naphthyl, anthracyl or phenanthryl ring; or $R_1$ is a heteroaryl radical which is unsubstituted or substituted by $C_1$–$C_6$alkyl, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$ with further substituents on the heteroaryl ring or with one of the carbon atoms of the heteroaryl ring; or $R_1$ is $C_2$–$C_{12}$alkenyl, $C_4$–$C_8$cycloalkenyl, or $C_6$–$C_{12}$bicycloalkenyl, with the proviso that the double bond (or the double bonds) of the radicals $C_2$–$C_{12}$alkenyl, $C_4$–$C_8$cycloalkenyl, or $C_6$–$C_{12}$bicycloalkenyl is (are) conjugated with the double bond substituted by $R_4$ and $R_5$; or, if m is zero, $R_1$ additionally is benzoyl, 2-furoyl, 2-thiophenecarbonyl, 2-pyridinecarbonyl or 2-pyrrolecarbonyl, wherein the radicals benzoyl, 2-furoyl, 2-thiophenecarbonyl, 2-pyridinecarbonyl or 2-pyrrolecarbonyl are unsubstituted or substituted by one or more of the radicals $C_1$–$C_{12}$alkyl, $C_1$–$C_4$haloalkyl, halogen, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$, with further substituents on the benzoyl, 2-furoyl, 2-thiophenecarbonyl, 2-pyridinecarbonyl or 2-pyrrolecarbonyl ring or with one of the carbon atoms of the benzoyl, 2-furoyl, 2-thiophenecarbonyl, 2-pyridinecarbonyl or 2-pyrrolecarbonyl ring; or, if m is zero, n is 1 and simultaneously $R_5$ is phenyl which is unsubstituted or substituted by one or more $C_1$–$C_{12}$alkyl, $C_1$–$C_4$haloalkyl, halogen, phenyl, $OR_6$, $NR_7R_8$, $SR_9$ and/or —S-phenyl, $R_1$ additionally is hydrogen or halogen;

$R'_1$ is vinylene, phenylene, naphthylene,

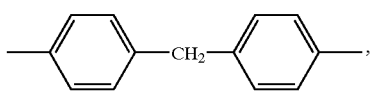

diphenylene or oxydiphenylene, wherein the radicals phenylene, naphthylene,

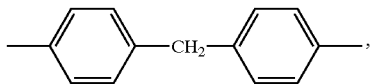

diphenylene and oxydiphenylene are unsubstituted or substituted by $C_1$–$C_{12}$alkyl;

$R_2$ is CN, $C_1$–$C_4$haloalkyl, $C_2$–$C_6$alkoxycarbonyl, phenoxycarbonyl, $C_1$–$C_6$alkyl-S(O)$_x$—, $C_6$–$C_{12}$aryl-S(O)x—, which is unsubstituted or substituted by $C_1$–$C_{12}$alkyl, or $R_2$ is $C_1$–$C_6$alkyl-SO$_2$O—, $C_6$–$C_{10}$aryl-SO$_2$O—, diphenyl-phosphinoyl or $R_2$ is benzoyl which is unsubstituted or substituted by CN, NO$_2$ or $C_1$–$C_4$haloalkyl;

x is 1 or 2;

$R_3$ is $C_1$–$C_{18}$alkylsulfonyl, phenyl-$C_1$–$C_3$alkylsulfonyl, camphorylsulfonyl, $C_1$–$C_{10}$haloalkylsulfonyl, phenylsulfonyl, naphthylsulfonyl, anthracylsulfonyl or phenanthrylsulfonyl, wherein the groups phenyl, naphthyl, anthracyl and phenanthryl of the radicals phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, NO$_2$, $C_1$–$C_{16}$alkyl, phenyl, $C_1$–$C_4$alkylthio, OR$_6$, COOR$_9$, $C_1$–$C_4$alkyl-OCO—, $R_9$OSO$_2$— and/or —NR$_7$R$_8$; or $R_3$ is $C_2$–$C_6$haloalkanoyl, halobenzoyl, triphenylsilyl, or a group

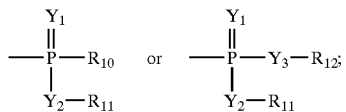

$Y_1$, $Y_2$ and $Y_3$ are independently of each other O or S;

$R'_3$ is $C_2$–$C_{12}$alkylenedisulfonyl, phenylenedisulfonyl, naphthylenedisulfonyl,

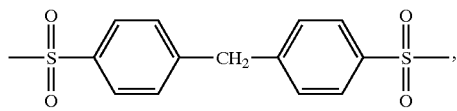

diphenylenedisulfonyl, or oxydiphenylenedisulfonyl, wherein the groups phenylene, naphthylene,

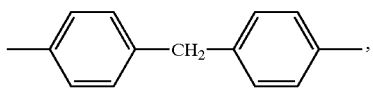

diphenylene and oxydiphenylene of the radicals phenylenedisulfonyl, naphthylenedisulfonyl,

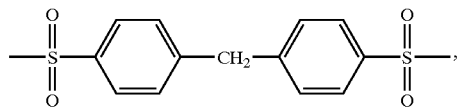

diphenylenedisulfonyl, or oxydiphenylenedisulfonyl are unsubstituted or substituted by $C_1$–$C_{12}$alkyl;

$R_4$ and $R_5$ are independently of each other hydrogen, halogen, $C_1$–$C_8$alkyl, $C_1$–$C_6$alkoxy, $C_1$–$C_4$haloalkyl, CN, NO$_2$, $C_2$–$C_6$alkanoyl, benzoyl, phenyl, —S-phenyl, OR$_6$, SR$_9$, NR$_7$R$_8$, $C_2$–$C_6$alkoxycarbonyl or phenoxycarbonyl, or $R_4$ and $R_5$ together are a direct bond;

$R_6$ is hydrogen, phenyl, $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl, or $R_6$ is $C_2$–$C_{12}$alkyl which is interrupted by one or more —O— or —S—, wherein the interrupted $C_2$–$C_{12}$alkyl is unsubtstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl;

$R_7$ and $R_8$ are independently of each other hydrogen or $C_1$–$C_{12}$alkyl which is unsubstituted or substituted by OH, $C_1$–$C_4$alkoxy, $C_1$–$C_{12}$alkylsulfonyl, phenylsulfonyl, (4-methyl-phenyl)sulfonyl and/or $C_1$–$C_6$alkanoyl; or $R_7$ and $R_8$ are $C_2$–$C_{12}$alkyl which is interrupted by one or more —O—, wherein the —O-interrupted $C_2$–$C_{12}$alkyl is unsubtstituted or substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or $R_7$ and $R_8$ are phenyl, $C_2$–$C_6$alkanoyl, benzoyl, $C_1$–$C_6$alkylsulfonyl, phenylsultonyl, (4-methylphenyl)sulfonyl, naphthylsulfonyl, anthracylsulfonyl or phenanthrylsulfonyl; or $R_7$ and $R_8$, together with the nitrogen atom to which they are bonded, form a 5-, 6- or 7-membered ring which may be interrupted by —O— or by —NR$_6$—;

$R_9$ is $C_1$–$C_{12}$ alkyl which is unsubstituted or substituted by OH and/or $C_1$–$C_4$alkoxy, or $R_9$ is $C_2$–$C_{12}$alkyl which is interrupted by one or more —O— or —S— and which interrupted $C_2$–$C_{12}$alkyl is unsubstituted or substituted by OH and/or $C_1$–$C_4$alkoxy;

$R_{10}$, $R_{11}$ and $R_{12}$ independently of one another are $C_1$–$C_6$alkyl which is unsubstituted or substituted by halogen; or $R_{10}$, $R_{11}$ and $R_{12}$ are phenyl which is unsubstituted or substituted by $C_1$–$C_4$alkyl or halogen; or $R_{11}$ and $R_{12}$ together are 1,2-phenylene or $C_2$–$C_6$alkylene which is unsubstituted or substituted by $C_1$–$C_4$alkyl or halogen;

with the proviso that if m and n both are 1, $R_4$ and $R_5$ both are hydrogen and $R_1$ is phenyl, $R_3$ is not p-tolylsulfonyl.

$C_1$–$C_{12}$alkyl is linear or branched and is, for example, $C_1$–$C_8$-, $C_1$–$C_6$- or $C_1$–$C_4$-alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl and octadecyl, preferably $C_1$–$C_4$alkyl, such as methyl, isopropyl or butyl.

$C_1$–$C_8$alkyl, $C_1$–$C_6$alkyl and $C_1$–$C_4$alkyl are likewise linear or branched and are, for example, as defined above up to the appropriate number of carbon atoms. Of interest are, for example, $C_1$–$C_8$-, especially $C_1$–$C_6$-, preferably $C_1$–$C_4$- alkyl, such as methyl or butyl. $C_2$–$C_{12}$alkyl, which is interrupted once or several times by —O—, is interrupted, for example, from one to five times, for example from one to three times or once or twice, by —O—. Accordingly, resulting structural units are for example: —O(CH$_2$)$_2$OH, —O(CH$_2$)$_2$OCH$_3$, —O(CH$_2$CH$_2$O)$_2$CH$_2$CH$_3$, —CH$_2$—O—CH$_3$, —CH$_2$CH$_2$—O—CH$_2$CH$_3$, —[CH$_2$CH$_2$O]$_y$—CH$_3$, wherein y=1–5, —(CH$_2$CH$_2$O)$_5$CH$_2$CH$_3$, —CH$_2$—CH(CH$_3$)—O—CH$_2$—CH$_2$CH$_3$ or —CH$_2$—CH(CH$_3$)—O—CH$_2$—CH$_3$, —O(CH$_2$)$_2$SCH$_3$, —(CH$_2$)$_2$SCH$_2$CH$_3$, or —O(CH$_2$)$_2$SCH$_2$CH$_3$. The interrupting O-atoms and/or S-atoms are non-successive.

$C_2$–$C_{12}$alkenyl radicals may be mono or polyunsaturated, linear or branched and are for example $C_2$–$C_8$-, $C_2$–$C_6$- or $C_2$–$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_4$–$C_8$cycloalkenyl, may have one or more double bonds and is for example $C_4$–$C_6$-cycloalkenyl or $C_6$–$C_8$-cycloalkenyl. Examples are cyclobutenyl, cyclopentenyl, cyclohexenyl or cyclooctenyl, especially cyclopentenyl and cyclohexenyl, preferably cyclohexenyl.

$C_6$–$C_{12}$bicycloalkenyl refers to a bicyclic alkenyl group, which may possess one or more double bonds and wherein the double bonds are either situated in the same ring, but may also be situated in both rings. If several double bonds are present in the bicyclus, the double bonds are conjugated or non-conjugated, preferably the double bonds are conjugated. At least one of the double bonds of the bicycloalkenyl radical is conjugated with the double bond of formula I, II, III which is substituted by the radicals $R_4$ and $R_5$. Examples are bicyclo[4.0.4]dodec-3,7-dien-5-yl, bicyclo[4.0.4]dodec-3-en-5-yl, bicyclo[4.0.4]dodec-4-en-6-yl, bicyclo[4.0.3]-non-3-en-5-yl, bicyclo[4.0.3]-non-4-en-6-yl, bicyclo[4.0.3]-non-7-en-8-yl, bicyclo[4.0.3]-non-8-en-7-yl, bicyclo[2.2.1]hept-2-en-3-yl, bicyclo[2.2.2]oct-2-en-3-yl, wherein the examples are referring to the following numbering

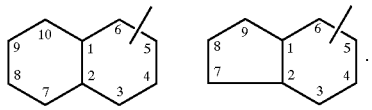

$C_2$–$C_{12}$alkylene is linear or branched and is, for example, $C_2$–$C_8$-, $C_2$–$C_6$- or $C_2$–$C_4$-alkylene. Examples are ethylene, propylene, butylene, pentylene, hexylene, heptylene, octylene, nonylene, decylene, undecylene and dodecylene. Preferred is $C_1$–$C_8$alkylene, especially $C_1$–$C_6$alkylene, preferably $C_1$–$C_4$alkylene, such as methylene or butylene.

$C_2$–$C_{12}$alkylenedisulfonyl accordingly is an alkylene radical as indicated above, which at both "yl"-moieties bears a sulfonyl group. Examples are —SO$_2$—(CH$_2$CH$_2$)$_z$—SO$_2$—, with z=1–6, e.g. —SO$_2$—CH$_2$CH$_2$—SO$_2$—, or —SO$_2$—CH(CH$_3$)CH$_2$—SO$_2$—.

Phenylenedisulfonyl, diphenylenedisulfonyl and oxy-diphenylendisulfonyl also bear the sulfonyl groups at the "yl" moiety. Accordingly, resulting structures are

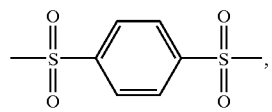

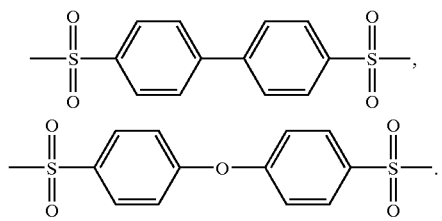

Substituted phenyl carries from one to five, for example one, two or three, especially one or two, substituents on the phenyl ring. The substitution is preferably in the 4-, 3,4-, 3,5- or 3,4,5-position of the phenyl ring.

When the radicals naphthyl, phenanthryl, heteroaryl and anthracyl are substituted by one or more radicals, they are, for example, mono- to penta-substituted, for example mono-, di- or tri-substituted, especially mono- or di-substituted.

When $R_1$ is a phenyl radical substituted by $OR_6$, $NR_7R_8$ and/or by $SR_9$ and the substituents $OR_6$, $NR_7R_8$ and $SR_9$ form 5- or 6-membered rings, via the radicals $R_6$, $R_7$, $R_8$ or $R_9$, with other substituents on the phenyl ring or with one of the carbon atoms of the phenyl ring, for example the following structural units are obtained

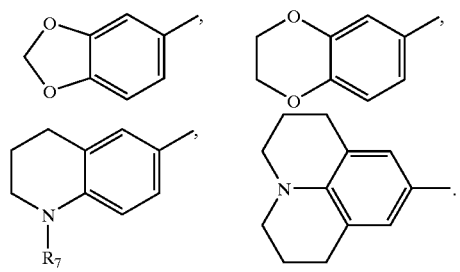

In the present application, the term "heteroaryl" denotes unsubstituted and substituted radicals, for example 3-thienyl, 2-thienyl,

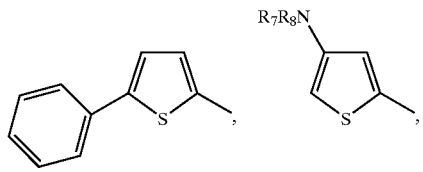

wherein $R_7$ and $R_8$ are as defined above, thianthrenyl, isobenzofuranyl, xanthenyl, phenoxanthiinyl,

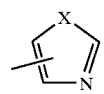

or

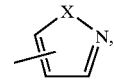

wherein X is S, O or $NR_7$ and $R_7$ is as defined above. Examples thereof are pyrazolyl, thiazolyl, oxazolyl, isothiazolyl or isoxazolyl. Also included are, for example, furyl, pyrrolyl, 1,2,4-triazolyl,

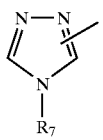

or 5-membered ring heterocycles having a fused-on aromatic group, for example benzimidazolyl, benzothienyl, benzofuranyl, benzoxazolyl and benzothiazolyl.

Other examples of "heteroaryls" are pyridyl, especially 3-pyridyl,

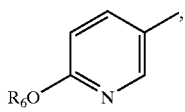

wherein $R_6$ is as defined above, pyrimidinyl, pyrazinyl, 1,3,5-triazinyl, 2,4-, 2,2- or 2,3-diazinyl, indolizinyl, isoindolyl, indolyl, indazolyl, purinyl, isoquinolyl, quinolyl, phenoxazinyl or phenazinyl. In this Application, the term "heteroaryl" also denotes the radicals thioxanthyl, xanthyl,

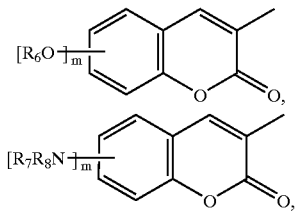

wherein $R_6$, $R_7$, $R_8$ and m are as defined above,

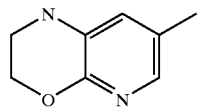

or anthraquinonyl. Each of the heteroaryls may carry the substituents indicated above or in claim 1.

Camphoryl is

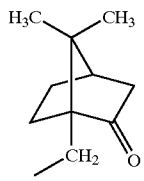

Oxydiphenylene is

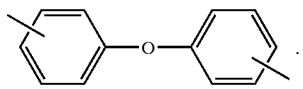

Diphenyiphosphinoyl is

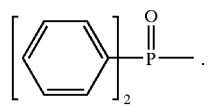

$C_1$–$C_6$alkanoyl is, for example, formyl, acetyl, propionyl, butanoyl or hexanoyl, especially acetyl.

$C_1$–$C_4$alkoxy is, for example, methoxy, ethoxy, propoxy and butoxy, it being possible for the alkyl radicals in alkoxy groups having more than two carbon atoms also to be branched.

$C_1$–$C_4$alkylhtio is for example, methylthio, ethylthio, propylthio and butylthio, it being possible for the alkyl radicals in alkylthio groups having more than two carbon atoms also to be branched.

$C_2$–$C_6$Alkoxycarbonyl is ($C_1$–$C_5$alkyl)-O—C(O)—, wherein $C_1$–$C_5$alkyl is as defined above up to the appropriate number of carbon atoms. Examples are methoxycarbonyl, ethoxycarbonyl, propoxycarbonyl, butoxycarbonyl or pentyloxycarbonyl, it being possible for the alkyl radicals in alkoxy groups having more than two carbon atoms also to be branched.

$C_1$–$C_{10}$Haloalkyl and $C_1$–$C_4$haloalkyl are $C_1$–$C_{10}$- and $C_1$–$C_4$-alkyl mono- or poly-substituted by halogen, $C_1$–$C_{10}$- and $C_1$–$C_4$-alkyl being, for example, as defined above. There are, for example, from one to three or one or two halogen substituents at the alkyl radical. Examples are chloromethyl, trichloromethyl, trifluoromethyl or 2-bromopropyl, especially trifluoromethyl or trichloromethyl.

$C_2$–$C_6$haloalkanoyl is ($C_1$–$C_5$haloalkyl)-C(O)—, wherein $C_1$–$C_5$haloalkyl is as defined above up to the appropriate number of carbon atoms. Examples are chloroacetyl, trichloroacetyl, trifluoroacetyl, pentafluoropropionyl, perfluorooctanoyl, or 2-bromopropionyl, especially trifluoroacetyl or trichloroacetyl.

Halobenzoyl is benzoyl which is mono- or poly-substituted by halogen and/or $C_1$–$C_4$haloalkyl, $C_1$–$C_4$-haloalkyl being as defined above. Examples are pentafluorobenzoyl, trichlorobenzoyl, trifluoromethylbenzoyl, especially pentafluorobenzoyl.

Halogen is fluorine, chlorine, bromine or iodine, especially chlorine or fluorine, preferably fluorine In a group $C_6$–$C_{10}$arylS(O)$_x$— which is unsubstituted or substituted by $C_1$–$C_{12}$alkyl, the aryl radical is for example phenyl, tolyl, dodecylphenyl or 1- or 2-naphthyl.

Phenyl-$C_1$–$C_3$alkyl is, for example, benzyl, 2-phenylethyl, 3-phenylpropyl, α-methylbenzyl or α,α-dimethylbenzyl, especially benzyl.

When $R_7$ and $R_8$ together with the nitrogen atom to which they are bonded form a 5-, 6- or 7-membered ring that may be interrupted by —O— or by —NR$_6$—, for example the following structures are obtained

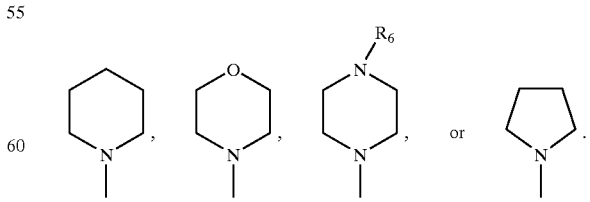

The definitions $C_1$–$C_{18}$alkylsulfonyl, phenyl-$C_1$–$C_3$alkylsulfonyl, camphorylsulfonyl, $C_1$–$C_{10}$haloalkylsulfonyl refer to the corresponding radicals $C_1$–$C_{18}$alkyl, phenyl-$C_1$–$C_3$alkyl, camphoryl and $C_1$–$C_{10}$haloalkyl, as described in detail above, being linked to a sulfonyl group (—$SO_2$—). Accordingly, also phenylsulfonyl, naphthylsulfonyl, anthracylsulfonyl and phenanthrylsulfonyl refer to the corresponding radicals linked to a sulfonyl group.

The terms "and/or" or "or/and" in the claims are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

Preference is given to compounds of formula I and II, wherein m is zero or 1;

n is 1;

$R_1$ is unsubstituted phenyl or phenyl which is substituted by $C_1$–$C_6$alkyl, phenyl, $OR_6$, $SR_9$, —S-phenyl, halogen and/or by $NR_7R_6$, it being possible for the substituents $OR_6$ and $NR_7R_8$ to form 5- or 6-membered rings, via the radicals $R_6$, $R_7$ and/or $R_8$ with further substituents of the phenyl ring, or with one of the carbon atoms of the phenyl ring; or $R_1$ is $C_4$–$C_8$cycloalkenyl or $C_6$–$C_{12}$bicycloalkenyl;

$R'_1$ is phenylene, naphthylene,

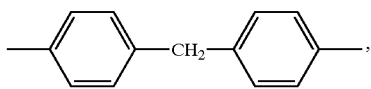

diphenylene or oxydiphenylene, wherein the radicals phenylene, naphthylene,

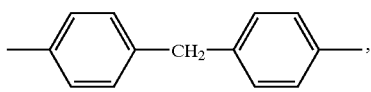

diphenylene and oxydiphenylene are unsubstituted or substituted by $C_1$–$C_{12}$alkyl.

Specifically preferred are compounds of formula I, wherein n is 1, m is zero or 1, $R_1$ is unsubstituted phenyl or phenyl substituted by $C_1$–$C_4$alkyl or $OR_6$; $R_2$ is CN; $R_3$ is $C_1$–$C_4$alkylsulfonyl; and $R_4$ and $R_5$ independently of each other are hydrogen or $C_1$–$C_4$alkyl.

Other interesting compounds are those of formula I, wherein n is 1; m is 0; $R_1$ is unsubstituted phenyl or phenyl substituted once or twice by $C_1$–$C_4$alkyl, $C_1$–$C_4$alkoxy or halogen; $R_2$ is CN or trifluoromethyl; $R_3$ is $C_1$–$C_{16}$alkylsulfonyl or unsubstituted or $C_1$–$C_4$alkyl-substituted phenylsulfonyl; $R_4$ and $R_5$ independently of each other are hydrogen, $C_1$–$C_4$alkyl, phenyl, $C_1$–$C_4$alkoxy or $C_2$–$C_6$alkoxycarbonyl.

Compounds of the formula I, wherein m is 0 and n is 1 are specifically preferred and in the following are referred to as compounds of the formula Ia

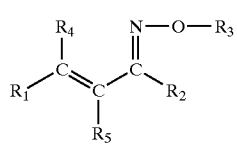

wherein $R_1$, $R_2$, $R_3$, $R_4$ and $R_5$ are as defined above.

Preferred are compounds of formula Ia, wherein $R_1$ is unsubstituted phenyl or phenyl substituted once or twice by $C_1$–$C_4$alkyl, $OR_6$ or halogen or $R_1$ is cyclohexenyl, furyl or thienyl;

$R_2$ is CN or trifluoromethyl;

$R_3$ is $C_1$–$C_{16}$alkylsulfonyl; camphorylsulfonyl; or phenylsulfonyl which is unsubstituted or substituted 1–5 times by $C_1$–$C_{12}$alkyl, $C_1$–$C_4$alkoxy, $C_1$–$C_4$haloalkyl, $C_1$–$C_4$alkylthio, $NO_2$ or halogen; or $R_3$ is —P(O)($OR_{11}$)($OR_{12}$);

$R_4$ and $R_5$ independently of each other are hydrogen, $C_1$–$C_4$alkyl, phenyl, $C_1$–$C_4$alkoxy or $C_2$–$C_6$alkoxycarbonyl;

$R_6$ is $C_1$–$C_4$alkyl or $C_1$–$C_4$alkylsulfonyl; and $R_{11}$, $R_{12}$ are $C_1$–$C_6$alkyl or phenyl.

Further compounds of interest are those wherein in the formula Ia, $R_1$ is a heteroaryl radical that is unsubstituted or mono- or poly-substituted by $C_1$–$C_6$alkyl, phenyl, $OR_6$, $SR_9$, —S-phenyl and/or by $NR_7R_8$, it being possible for the substituents $OR_6$ and $NR_7R_8$ to form 5- or 6-membered rings, via the radicals $R_6$, $R_7$ and/or $R_8$, with further substituents or with one of the carbon atoms of the heteroaryl ring, or $R_1$ is benzoyl, 2-furoyl, 2-thiophenecarbonyl, 2-pyridinecarbonyl or 2-pyrrolecarbonyl, the radicals benzoyl, 2-furoyl, 2-thiophenecarbonyl, 2-pyridinecarbonyl or 2-pyrrolecarbonyl being unsubstituted or substituted by one or more of the radicals $C_1$–$C_{12}$alkyl, $C_1$–$C_4$haloalkyl, halogen, phenyl, $OR_6$, $NR_7R_8$, $SR_9$ and/or —S-phenyl.

Further compounds of interest are those of the formula II, wherein $R'_1$ is phenylene, naphthylene,

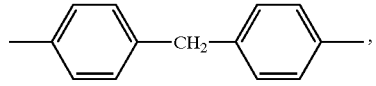

diphenylene or oxydiphenylene, the radicals phenylene, naphthylene,

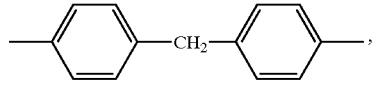

diphenylene and oxydiphenylene being unsubstituted or substituted by $C_1$–$C_{12}$alkyl;

Mention should be made of compounds of formula Ia and II wherein $R_2$ is CN, $C_2$–$C_6$alkoxycarbonyl, $C_1$–$C_4$haloalkyl, $C_1$–$C_6$alkylS(O)$_x$—, unsubstituted $C_6$–$C_{10}$arylS(O)$_x$— or $C_6$–$C_{10}$arylS(O)$_x$— which is substituted by $C_1$–$C_{12}$alkyl.

Most preferred compounds are those of formula Ia, where $R_1$ is phenyl (optionally substituted as defined above) or a heteroaryl radical (optionally substituted as defined above) and $R_2$ is CN.

Preference is given especially to compounds of formula Ia and II wherein $R_6$ is $C_1$–$C_6$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or by $C_2$–$C_6$alkanoyl or $R_6$ is $C_2$–$C_6$alkyl which is interrupted by —O—, wherein the interrupted $C_2$–$C_6$alkyl radical is unsubstituted or substituted by OH, $C_1$–$C_4$alkoxy, $C_1$–$C_{12}$alkylsulfonyl, phenylsulfonyl, (4-methylphenyl)sulfonyl and/or by $C_2$–$C_6$alkanoyl.

Preference is given also to compounds of formula Ia and II wherein $R_3$ is $C_1$–$C_{18}$alkylsulfonyl, $C_1$–$C_{10}$haloalkylsulfonyl, or phenylsulfonyl which is unsubstituted or substituted by halogen, $NO_2$, $C_1$–$C_4$haloalkyl, $C_1$–$C_{16}$alkyl or $C_1$–$C_{12}$alkyl, $OR_6$, $COOR_9$ and/or by —OCO—$C_1$–$C_4$alkyl.

Preference is given likewise compounds of formula Ia and II wherein $R_4$ and $R_5$ are independently of each other hydrogen, halogen, $C_1$–$C_6$alkyl, phenyl, $C_1$–$C_6$alkoxy or $C_2$–$C_6$alkoxycarbonyl;

$R_7$ and $R_8$ are independently of each other hydrogen or $C_1$–$C_{12}$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or by $C_1$–$C_6$alkanoyl; or are $C_2$–$C_{12}$alkyl which is interrupted by —O—, wherein the interrupted $C_2$–$C_{12}$alkyl is unsubstituted or substituted by OH, $C_1$–$C_4$alkoxy, $C_1$–$C_{12}$alkylsulfonyl, phenylsulfonyl, (4-methylphenyl)sulfonyl and/or by $C_1$–$C_6$alkanoyl; or $R_7$ and $R_8$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl; or $R_7$ and $R_8$, together with the nitrogen atom to which they are bonded, form a 5-, 6- or 7-membered ring which may be interrupted by —O— or by —$NR_6$—; and $R_9$ is $C_1$–$C_{12}$alkyl which is unsubstituted or substituted by OH and/or by $C_1$–$C_4$alkoxy or is $C_2$–$C_{12}$alkyl which is interrupted by —O—, wherein the interrupted $C_2$–$C_{12}$alkyl is unsubstituted or substituted by OH and/or $C_1$–$C_4$alkoxy.

Specific examples of compounds according to the present invention are

2-Methylsulfonyloxyimino-4-phenyl-but-3-enenitrile;
2-Methylsulfonyloxyimino-4-p-tolyl-but-3-enenitrile;
2-Methylsulfonyloxyimino-4-(4-methoxy-phenyl)-but-3-enenitrile;
2-Methylsulfonyloxyimino-3-methyl-4-phenyl-but-3-enenitrile;
2-Methylsulfonyloxyimino-3-oxo-5-phenyl-pent-4-enenitrile;
4-Cyano-4-(p-tolylsulfonyloxyimino)-2-phenyl-but-2-enoic acid ethyl ester;
4-Cyclohex-1-enyl-2-methylsulfonyloxyimino-but-3-enenitrile;
1,1,1-Trifluoro-4-(4-methylsulfanyl-phenyl)-but-3-en-2-one O-(10-camphorsulfonyl)-oxime;
1,1,1-Trifluoro-4-(4-methoxy-phenyl)-but-3-en-2-one O-(p-tolylsulfonyl)-oxime;
2-(4-Chloro-benzylidene)-3-methylsulfonyloxyimino-succinonitrile;
2-Octylsulfonyloxyimino-4-(2-methoxy-phenyl)-but-3-enenitrile;
2-Benzoyl-4-methylsulfonyloxyimino-3-phenyl-pent-2-enedinitrile;
2-Dodecylsulfonyloxyimino-4-thiophen-2-yl-but-3-enenitrile;
4-Furan-2-yl-2-isopropylsulfonyloxyimino-but-3-enenitrile;
3-Hexyl-2-diphenylphosphoryloxyimino-4-phenyl-but-3-enenitrile;
4-{4-[4-(3-Cyano-3-butylsultonyloxyimino-propenyl)-benzenesultonyl]-phenyl}-2-butylsulfonyloxyimino-but-3-enenitrile;
4-[4'-(3-Cyano-3-(p-tolylsulfonyloxyimino)-propenyl)-biphenyl-4-yl]-2-(p-tolylsulfonyloxyimino)-but-3-enenitrile;
4-{4-[4-(3-Cyano-3-methylsulfonyloxyimino-propenyl)-phenoxy]-phenyl}-2-methylsulfonyloxyimino-but-3-enenitrile;
2-Pentafluorophenylsulfonyloxyimino-4-phenyl-but-3-ynenitrile;
2-Ethylsulfonyloxyimino-3-(3-methoxy-phenyl)-but-3-enenitrile;
4-{4-[4-(3-Cyano-3-methanesulfonyloxyimino-propenyl)-benzyl]-phenyl}-2-methanesultonyloxyimino-but-3-enenitrile;
2-[4'-(1-Cyano-3-p-toly-allylideneaminooxysulfonyl)-biphenyl-4-ylsulfonyloxyimino]-4-p-tolyl-but-3-enenitrile.

The invention also relates to mixtures of isomeric forms of the compounds of formula I, Ia, II and III. The double bond of the oximino group can exist in both the syn (cis, Z) and the anti (trans, E) form or as mixtures of the two geometrical isomers. In addition, the n double bonds of formulae I, II and III can, depending on the substituents $R_4$ and $R_5$, exhibit two (Z and E)) configurations. In the present invention, both the individual geometrical isomers and any mixtures of two or more geometrical isomers can be used.

Unsaturated oxime esters (of formulae I, Ia, II and III) can be prepared by methods described in the literature, for example by reacting suitable free oximes ($R_3$ and $R'_3$=H) with the desired (for example, sulfonic) acid halides (for example, $R_3Cl$ or Cl—$R'_3$—Cl).

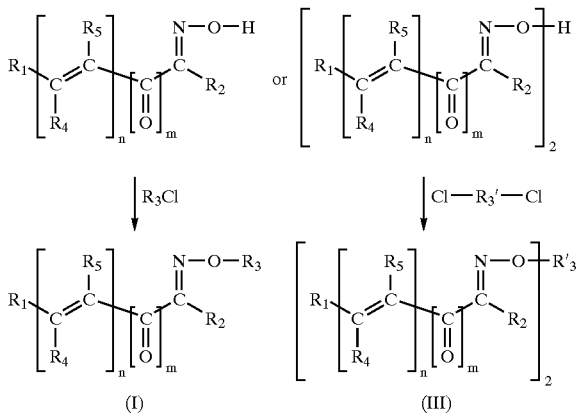

$R_1$, $R_2$, $R_3$, $R_3'$, $R_4$, $R_5$, n and m are defined as described above.

These reactions are carried out in an inert solvent such as toluene, tetrahydrofuran (THF) or dimethylformamide (DMF) in the presence of a base, for example a tertiary amine, such as triethylamine, or by reaction of the salt of an oxime with the desired acid chloride. These methods are disclosed, for example, in EP 48615. The sodium salts of oximes can be obtained, for example, by reacting the oxime in question with a sodium alcoholate in dimethylformamide.

The starting unsaturated oximes ($R_3$=H) can be prepared in numerous ways, which are known to the person skilled in the art, for example by the nitrosation of "active" methylene groups with nitrous acid or an alkyl nitrite. Both alkaline conditions, as described for example in Organic Syntheses coll. Vol. VI (J. Wiley & Sons, New York, 1988), pp 199 and 840, and acidic conditions, as described, for example, in Organic Synthesis col. Vol V, pp 32 and 373, coll. Vol. III, pp 191 and 513, coll. Vol.II, pp. 202, 204 and 363, are suitable for the preparation of the oximes used as starting materials in the invention. Nitrous acid is usually generated from sodium nitrite. The alkyl nitrite can be for example methyl nitrite, ethyl nitrite, isopropyl nitrite, butyl nitrite, isoamyl nitrite. Another example is the oximation of cinnamaldehydes (*Synthesis* 1994, 573) followed by cyanation (*J. Org. Chem.* 1993, 58, 2075). The most useful intermediates for the preparation of the unsaturated oximes of the invention are for example cinnamaldehyde derivatives and 4-aryl-but-3-ene nitriles. These intermediates are obtained by various methods depending on the particular structure desired. Examples of useful synthetic methods applicable to the synthesis of the intermediates are the condensation of aromatic aldehydes with acetaldehyde (*Arch. Pharm.* 1996, 329, 125), the cyanohydrin ester formation followed by reduction (*Synthesis* 1996, 1188; *J. Org. Chem.* 1983, 48, 3545), the Wittig/Horner reactions (*Chem. Pharm. Bull.* 1985, 33, 3558; *Bull. Soc. Chim. Fr.* 1974, 2065; J. Chem. Soc. Perkin Trans. 2, 1992, 1207), and the Heck reaction (R. F. Heck, Palladium Reagents in Organic Syntheses, Academic Press, London, 1985; *J. Chem. Soc.* 1993, 1943).

Oximes can also be obtained by reacting a suitable carbonyl or thionylcarbonyl compound with hydroxylamine or a hydroxylammonium salt.

The invention relates also to the use of compounds of formulae I, II and III as described above, as photoinitiators for compounds that can be crosslinked under the action of an acid and/or as solubility inhibitors for compounds the solubility of which is altered under the action of an acid, as well as to a method of crosslinking compounds which can be crosslinked under the action of an acid, which method comprises adding a compound of formula I, II and/or III as described above to the above-mentioned compounds and irradiating imagewise or over the whole area with light having a wavelength in the range of 180–1500 nm.

In photocrosslinkable compositions, the unsaturated oxime derivatives of the invention act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Compositions using pH sensitive dyes or latent pigments in combination with oxime derivatives according to the invention can be used as indicators for electromagnetic radiation, such as gamma radiation, electron beams, UV- or visible light, or simple throw away dosimeters. Especially for light, that is invisible to the human eye, like UV- or IR-light, such dosimeters are of interest.

Finally, oxime derivatives which are sparingly soluble in an aqueous-alkaline developer can be rendered soluble in the developer by means of light-induced conversion into the free acid, with the result that they can be used as solubility inhibitors in combination with suitable film-forming resins.

The invention therfore also pertains to a composition comprising
a) at least one compound that can be crosslinked under the action of an acid and/or
b) at least one compound the solubility of which is altered under the action of an acid and
c) as latent acid photoinitiator, at least one compound of the formulae I, II or III as described above.

These compositions may in addition to component c) comprise further photoinitiators, sensitizers and/or additives.

Resins which can be crosslinked by acid catalysis are, for example, mixtures of polyfunctional alcohols or hydroxy-group-containing acrylic and polyester resins, or partially hydrolysed polyvinylacetals or polyvinyl alcohols with polyfunctional acetal derivatives. Under certain conditions, for example the acid-catalysed self-condensation of acetal-functionalised resins is also possible.

In addition, oximesulfonates of formula I, II and III can be used, for example, as hardeners, which can be activated by light, for siloxane group-containing resins. These resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. That type of polycondensation of polysiloxanes is described, for example, in J. J. Lebrun, H. Pode, Comprehensive Polymer Science, Vol. 5, p. 593, Pergamon Press, Oxford, 1989.

It is desirable in these reactions for the acid to be released when irradiated with light of various wavelengths. Surprisingly, it has been found that the new unsaturated oxime derivatives according to the invention are thermally and chemically stable, exhibit very high light sensitivity, and are capable of releasing the acid when irradiated with light. In addition the compounds are rapidly bleached after exposure to light, a property which is very helpful for homogeneous generation of the acid throughout the entire thickness of the compositions irradiated with the light. This property is used for the curing of thick layers or the production of colourless articles with visible light.

The new unsaturated oxime derivatives of formula I, II and III, as already mentioned above can be used as hardeners, which can be activated by light, for acid-curable resins. Suitable acid-curable resins are all resins the curing of which can be accelerated by acid catalysts, such as aminoplasts or phenolic resole resins. These resins are especially melamine, urea, epoxy, phenolic, acrylic, polyester and alkyd resins, but especially mixtures of acrylic, polyester or alkyd resins with a melamine resin. Also included are modified surface-coating resins, such as acrylic-modified polyester and alkyd resins. Examples of individual types of resins that are covered by the expression acrylic, polyester and alkyd resins are described, for example, in Wagner, Sarx/Lackkunstharze (Munich, 1971), pages 86 to 123 and 229 to 238, or in Ullmann/Encyclopädie der techn. Chemie, 4th Edition, Volume 15 (1978), pages 613 to 628, or Ullmann's Encyclopedia of Industrial Chemistry, Verlag Chemie, 1991, Vol. 18, 360 ff., Vol. A19, 371 ff.

The composition can for example be used as a surface coating. The surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxy-group-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. As already mentioned above, for example polysiloxanes can also be crosslinked using acid catalysis. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-2H-pyran (dimeric acrolein) or the 3,4-dihydro-2H-pyran-2-carboxylic acid ester of 2-hydroxymethyl-3,4-dihydro-2H-pyran; vinyl esters, such as vinyl acetate and vinyl stearate, mono- and di-olefins, such as α-methylstyrene, N-vinylpyrrolidone or N-vinylcarbazole.

For certain purposes, resin mixtures having monomeric or oligomeric constituents containing polymerisable unsaturated groups are used. Such surface coatings can also be cured using compounds of formula I, II or III. In that process, a) radical polymerisation initiators or b) photoinitiators can additionally be used. The former initiate polymerisation of the unsaturated groups during heat treatment, the latter during UV irradiation.

According to the invention, the compositions, which can be activated by light, may comprise further photoinitiators, sensitisers and/or additives in addition to component c), or the compounds of formula I, II or III can be used together with further photoinitiators, sensitisers and/or additives.

Examples of additional photoinitiators are radical photoinitiators, such as those from the class of the benzophenones, acetophenone derivatives, such as α-hydroxycycloalkylphenyl ketone, dialkoxyacetophenone, α-hydroxy-acetophenone or α-amino-acetophenone, 4-aroyl-1,3-dioxolans, benzoin alkyl ethers and benzil ketals, monoacylphosphine oxides, bisacylphosphine oxides or titanocenes, camphor quinone, phenylglyoxalic esters and derivatives thereof, dimeric phenylglyoxalic esters, peresters, e.g. benzophenone tetracarboxylic peresters as described for example in EP 126541, ferrocenium compounds, or titanocenes, e.g. bis(cyclopentadienyl)-bis(2, 6-difluoro-3-pyrryl-phenyl)titanium.

Examples of especially suitable additional photoinitiators are: 1-(4-dodecylbenzoyl)-1-hydroxy-1-methyl-ethane, 1-(4-isopropylbenzoyl)-1-hydroxy-1-methyl-ethane, 1-benzoyl-1-hydroxy-1-methyl-ethane, 1-[4-(2-hydroxyethoxy)-benzoyl]-1-hydroxy-1-methyl-ethane, 1-[4-(acryloyloxyethoxy)-benzoyl]-1-hydroxy-1-methyl-ethane, diphenyl ketone, phenyl-1-hydroxycyclohexyl ketone, (4-morpholinobenzoyl)-1-benzyl-1-dimethylamino-propane, 1-(3,4-dimethoxyphenyl)-2-benzyl-2-dimethylamino-butan-1-one, (4-methylthiobenzoyl)-1-methyl-1-morpholino-ethane, benzil dimethyl ketal, bis(cyclopentadienyl)-bis(2,6-difluoro-3-pyrryl-phenyl) titanium, trimethylbenzoyldiphenylphosphine oxide, bis(2, 6-dimethoxy-benzoyl)-(2,4,4-trimethyl-pentyl)-phosphine oxide, bis(2,4,6-trimethylbenzoyl)-2,4-dipentyloxyphenyl-phosphine oxide or bis(2,4,6-trimethylbenzoyl)phenyl-phosphine oxide. Further suitable additional photoinitiators are to be found in U.S. Pat. No. 4,950,581, column 20, line 35 to column 21, line 35. Other examples are trihalomethyltriazine derivatives or hexaarylbisimidazolyl compounds, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]-triazine, 2-methyl-4,6-bis-trichloromethyl-[1,3,5]triazine, hexaarylbisimidazole/coinitiators systems, e.g. ortho-chlorohexaphenyl-bisimidazole combined with 2-mercaptobenzthiazole. Further examples for additional photoinitiators are borate compounds, as for example described in U.S. Pat. No. 4,772,530, EP 775706, GB 2307474, GB 2307473 and GB 2304472. The borate compounds preferably are used in combination with electron acceptor compounds, such as, for example dye cations, or thioxanthone derivatives.

Further examples of additional photoinitiators are, for example, peroxide compounds, e.g. benzoyl peroxide (other suitable peroxides are described in U.S. Pat. No. 4,950,581, column 19, lines 17–25) or cationic photoinitiators, such as aromatic sulfonium or iodonium salts, such as those to be found in U.S. Pat. No. 4,950,581, column 18, line 60 to column 19, line 10, or cyclopentadienyl-arene-iron(II) complex salts, for example ($\eta^6$-isopropylbenzene)($\eta^5$-cyclopentadienyl)-iron(II) hexafluorophosphate.

The surface coatings may be solutions or dispersions of the surface-coating resin in an organic solvent or in water, but they may also be solventless. Of special interest are surface coatings having a low solvent content, so-called "high solids surface coatings", and powder coating compositions. The surface coatings may be clear lacquers, as used, for example, in the automobile industry as finishing lacquers for multilayer coatings. They may also comprise pigments and/or fillers, which may be inorganic or organic compounds, and metal powders for metal effect finishes.

The surface coatings may also comprise relatively small amounts of special additives customary in surface-coating technology, for example flow improvers, thixotropic agents, leveling agents, antifoaming agents, wetting agents, adhesion promoters, light stabilisers, antioxidants, or sensitisers. UV absorbers, such as those of the hydroxyphenyl-benzotriazole, hydroxyphenyl-benzophenone, oxalic acid amide or hydroxyphenyl-s-triazine type may be added to the compositions according to the invention as light stabilisers. Individual compounds or mixtures of those compounds can be used with or without the addition of sterically hindered amines (HALS).

Examples of such UV absorbers and light stabilisers are 1. 2-(2'-Hydroxyhenyl)-benzotriazoles, such as 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)phenyl)-benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazote, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethyl-hexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2-isooctyloxycarbonylethyl)phenyl-benzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]-benzotriazole with polyethylene glycol 300; [R—CH$_2$CH$_2$—COO(CH$_2$)$_3$]$_2$— wherein R=3'-tert-butyl-4'-hydroxy-5'-2H-benzotriazol-2-yl-phenyl.

2. 2-Hydroxybenzophenones, such as the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.
3. Esters of unsubstituted or substituted benzoic acids, such as 4-tert-butyl-phenyl salicylate, phenyl salicylate, octylphenyl salicylate, dibenzoylresorcinol, bis(4-tert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.
4. Acrylates, such as α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.
5. Sterically hindered amines, such as bis(2,2,6,6-tetramethyl-piperidyl)sebacate, bis(2,2,6,6-tetramethyl-piperidyl)succinate, bis(1,2,2,6,6-pentamethylpiperidyl)sebacate, nbutyl-3,5-di-tert-butyl-4-hydroxybenzyl-malonic acid bis(1,2,2,6,6-pentamethylpiperidyl)ester, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, condensation product of N,N'-bis(2,2,6,6-tetra-methyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-amino-propylamino)ethane, condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione.
6. Oxalic acid diamides, such as 4,4'-dioctyloxy-oxanilide, 2,2'-diethoxy-oxanilide, 2,2'-di-octyloxy-5,5'-di-tert-butyl-oxanilide, 2,2'-didodecyloxy-5,5'-di-tert-butyl-oxanilide, 2-ethoxy-2'-ethyl-oxanilide, N,N'-bis(3-dimethylaminopropyl)oxalamide, 2-ethoxy-5-tert-butyl-2'-ethyloxanilide and a mixture thereof with 2-ethoxy-2'-ethyl-5,4'-di-tert-butyl-oxanilide, mixtures of o- and p-methoxy- and of o- and p-ethoxy-di-substituted oxanilides.
7. 2-(2-Hydroxyphenyl)-1,3,5-triazines, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-di-hydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethyl-phenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl-/tridecyl-oxy-(2-hydroxypropyl)oxy-2-hydroxy-phenyl]-4,6-bis(2,4-dimethylphenyl)-1,3,5-triazine.
8. Phosphites and phosphonites, such as triphenyl phosphite, diphenyl alkyl phosphites, phenyl dialkyl phosphites, tris(nonylphenyl)phosphite, trilauryl phosphite, trioctadecyl phosphite, distearyl-pentaerythritol diphosphite, tris(2,4-di-tert-butylphenyl)phosphite, diisodecylpentaerythritol diphosphite, bis(2,4-di-tert-butylphenyl) pentaerythritol diphosphite, bis(2,6-di-tert-butyl-4-methylphenyl)pentaerythritol diphosphite, bisisodecyloxy-pentaerythritol diphosphite, bis(2,4-di-tert-butyl-6-methylphenyl)pentaerythritol diphosphite, bis-(2,4,6-tri-tert-butylphenyl)pentaerythritol diphosphite, tristearyl-sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl)methyl phosphite, bis(2,4-di-tert-butyl-6-methylphenyl)ethyl phosphite.

Such light stabilisers can also be added, for example, to an adjacent surface-coating layer from which they gradually diffuse into the layer of stoving lacquer to be protected. The adjacent surface-coating layer may be a primer under the stoving lacquer or a finishing lacquer over the stoving lacquer.

It is also possible to add to the composition, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat. No. 4,017,652), 3-acyl-coumarins (as described, for example, in U.S. Pat. No. 4,366,228, EP 738928, EP 22188), keto-coumarines (as described e.g. in U.S. Pat. No. 5,534,633, EP 538997, JP 8272095-A), styryl-coumarines (as described e.g. in EP 624580), 3-(aroylmethylene)-thiazolines, thioxanthones, condensed aromatic compounds, such as perylene, aromatic amines (as described, for example, in U.S. Pat. No. 4,069,954 or WO 96/41237) or cationic and basic colourants (as described, for example, in U.S. Pat. No. 4,026,705), for example eosine, rhodanine and erythrosine colourants, as well as dyes and pigments as described for example in JP 8320551-A, EP 747771, JP 7036179-A, EP 619520, JP 6161109-A, JP 6043641, JP 6035198-A, WO 93/15440, EP 568993, JP 5005005-A, JP 5027432-A, JP 5301910-A, JP 4014083-A, JP 4294148-A, EP 359431, EP 103294, U.S. Pat. No. 4,282,309, EP 39025, EP 5274, EP 727713, EP 726497 or DE 2027467.

Other customary additives are—depending on the intended use—optical brighteners, fillers, pigments, e.g. latent pigments, dyes, colourants, wetting agents or flow improvers.

For curing thick and pigmented coatings, the addition of micro glass beads or powdered glass fibres, as described in U.S. Pat. No. 5,013,768, is suitable. Other examples of additional photoinitiators or additives have been given hereinbefore.

The choice of additive is made depending on the field of application and on properties required for this field. The additives described above are customary in the art and accordingly are added in amounts which are usual in the respective application.

Oximesulfonates can also be used, for example, in hybrid systems. These systems are based on formulations that are full cured by two different reaction mechanisms. Examples thereof are systems that comprise components that are capable of undergoing an acid-catalysed crosslinking reaction or polymerisation reaction, but that also comprise further components that crosslink by a second mechanism. Examples of the second mechanism are radical full cure, oxidative crosslinking or humidity-initiated crosslinking. The second curing mechanism may be initiated purely thermally, if necessary with a suitable catalyst, or also by means of light using a second photoinitiator.

If the composition comprises a radically crosslinkable component, the curing process, especially of compositions that are pigmented (for example with titanium dioxide), can also be assisted by the addition of a component that is radical-forming under thermal conditions, such as an azo compound, for example 2,2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP 245639. The addition of redox initiators, such as cobalt salts, enables the curing to be assisted by oxidative crosslinking with oxygen from the air.

The surface coating can be applied by one of the methods customary in the art, for example by spraying, painting on or immersion. When suitable surface coatings are used, electrical application, for example by electroimmersion coating, is also possible. After drying, the surface coating film is irradiated. If necessary, the surface coating film is then fully cured by means of heat treatment.

The compounds of formulae I, II or III can also be used for curing mouldings made from composites. A composite consists of a self-supporting matrix material, for example a glass fibre fabric, impregnated with the photocuring formulation.

Resist systems can be prepared by image-wise irradiation of systems comprising compounds of formulae I, II or III, followed by a developing step. As already mentioned above, compounds of formulae I, II or III can be used as photosensitive acid donors in a photoresist.

The invention accordingly relates also to a photoresist comprising as photosensitive acid donor at least one oximesulfonate compound of formulae I, II or III.

The difference in solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive. If, on the other hand, those components reduce the solubility of the composition after irradiation, the resist is negative.

The invention accordingly relates also to a negative photoresist and to a positive photoresist.

The oximesulfonates of formulae I, II or III can also be used in chemically amplified resists. A chemically amplified photoresist is understood to be a resist composition the photosensitive component of which, when irradiated, provides only that amount of acid that is required to catalyse a chemical reaction of at least one acid-sensitive component of the resist, as a result of which the ultimate differences in solubility between irradiated and non-irradiated areas of the photoresist first develop.

The invention accordingly relates also to a chemically amplified photoresist.

Subject of the invention further is the use of a compound of the formula I or II as photosensitive acid donor in a photoresist.

Such resists exhibit an outstanding lithographic sensitivity to radiation of different wavelength, since compounds of formulae I, II or III can be easily tuned over a broad range of the electromagnetic spectrum. The photoresists according to the invention have excellent lithographic properties, especially a high sensitivity, and homogeneous exposure-conditions over the whole resist thickness due to the fact that the optical absorption is bleached upon irradiation.

Acid-sensitive components that produce a negative resist characteristic are especially compounds that, when catalysed by acid (the acid formed during irradiation of the compounds of formulae I, II or III), are capable of undergoing a crosslinking reaction with themselves and/or with one or more further components of the composition. Compounds of that type are, for example, the known acid-curable resins, such as, for example, acrylic, polyester, alkyd, melamine, urea, epoxy and phenolic resins or mixtures thereof. Amino resins, phenolic resins and epoxy resins are very suitable. Acid-curable resins of that type are generally known and are described, for example, in Ullmann's Encyclopädie der technischen Chemie, 4th Edition, Vol. 15 (1978), p. 613–628. The crosslinker components should generally be present in a concentration of from 2 to 40, preferably from 5 to 30, percent by weight, based on the total solids content of the negative composition.

Especially preferred as acid-curable resins are amino resins, such as non-etherified or etherified melamine, urea, guanidine or biuret resins, especially methylated melamine resins or butylated melamine resins, corresponding glycolurils and urones. There are to be understood by resins in this context both customary technical mixtures, which generally also comprise oligomers, and pure and high purity compounds. N-Methoxymethyl melamine and tetramethoxymethyl glucoril and N,N'-dimethoxymethylurone are the acid-curable resins given the greatest preference.

The concentration of the compound of formula I, II or III in negative resists is in general from 0.1 to 30, preferably up to 20, percent by weight, likewise based on the total solids content of the compositions. From 1 to 15 percent by weight is especially preferred.

Where appropriate, the negative compositions may additionally comprise a film-forming polymeric binder. That binder is preferably an alkali-soluble phenolic resin. Well suited for that purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$–$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl) propane. Also suitable are homo- and co-polymers based on ethylenically unsaturated phenols, for example homopolymers of vinyl- and 1-propenyl-substituted phenols, such as p-vinylphenol or p-(1-propenyl)phenol or copolymers of these phenols with one or more ethylenically unsaturated materials, for example styrenes. The amount of binder should generally be from 30 to 99 percent by weight, e.g. 30 to 95 percent by weight or 40 to 80 percent by weight, preferably, from 40 to 95 percent by weight.

The invention thus includes, as a special embodiment, as already mentioned above, negative, alkali-developable photoresists, comprising an oximesulfonate of formula I, II or III as described above, an alkali-soluble phenolic resin as binder and a component that when catalysed by an acid undergoes a crosslinking reaction with itself and/or with the binder. An especially preferred form of that negative resist comprises from 1 to 15 percent by weight oximesulfonate, from 40 to 95 percent by weight of a phenolic resin as binder, for example one of those mentioned above, and from 0.5 to 30 percent by weight of a melamine resin as crosslinking agent, the percentages relating to the solids content of the composition. With novolak or especially with polyvinyl phenol as binder, a negative resist having especially good properties is obtained.

Oximesulfonates can also be used as acid generators, which can be activated photochemically, for the acid-catalysed crosslinking of, for example, poly(glycidyl) methacrylates in negative resist systems. Such crosslinking reactions are described, for example, by Chae et al. in Pollimo 1993, 17(3), 292.

Monomeric or polymeric compounds that are alkali-insoluble but are cleaved in the presence of acid, or are capable of being rearranged intramolecularly, in such a manner that reaction products remain that are soluble in a customary alkaline developer and/or that cause an otherwise alkali-insoluble and acid-resistant additional binder to become soluble in the developer, produce a positive characteristic in photoresist compositions according to the invention. Substances of that type are referred to hereinafter as solution inhibitors.

As already indicated hereinbefore, the invention therefore includes, as a further special embodiment, positive alkaline-developable photoresists, comprising a compound of formula I, II or III and at least one compound that substantially prevents the composition from dissolving in an alkaline developer, but that can be cleaved in the presence of an acid in such a manner that reaction products remain that are soluble in the developer and/or that cause an acid-resistant additional binder that would otherwise be virtually insoluble in the developer to dissolve in the developer.

There may be used as solution inhibitors monomeric and polymeric organic compounds having functional groups that would be soluble per se in an alkaline medium, for example aromatic hydroxy groups, carboxylic acid groups, secondary amino groups and keto or aldehyde groups, but that have been chemically so altered by reaction with a suitable compound that they are insoluble in aqueous alkali, the protecting groups formed in the mentioned reaction being capable of being cleaved again by acid catalysis in such a manner that the functional groups are recovered in their original form.

For the protection of hydroxy groups, carboxylic acid groups or secondary amino groups there are suitable, for example, dihydrofuran or 3,4-dihydropyran and the derivatives thereof, benzyl halides, alkyl halides, haloacetic acid, haloacetic acid esters, chlorocarbonic acid esters, alkylsulfonyl halides, aromatic sulfonyl halides, dialkyl dicarbonates or trialkylsilyl halides, it being possible for the reactions to form the protected derivatives to be carried out in known manner. Customary conversion into ketals and acetals is suitable for protecting keto and aldehyde groups.

Such chemically amplified positive resist systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

In positive resists of the mentioned type a film-forming, polymeric solution inhibitor can either be the only binder in the photoresist or can be used in admixture with an acid-inert binder and, where appropriate, a monomeric solution inhibitor.

Examples of acid-inert binders are novolaks, especially those based on o-, m- or p-cresol and formaldehyde, also poly(p-hydroxystyrene), poly(p-hydroxy-α-methylstyrene) and copolymers of p-hydroxystyrene, p-hydroxy-α-methylstyrene and acetoxystyrene.

Examples of polymeric solution inhibitors are novolaks, especially those based on o-, m- or p-cresol and formaldehyde, poly(p-hydroxystyrene), poly(p-hydroxy-α-methylstyrene), copolymers of p-hydroxystyrene or p-hydroxy-α-methylstyrene and acetoxystyrene or acrylic acid and/or methacrylic acid and (meth)acrylic acid esters, which are reacted in known manner with dihydrofuran, 3,4-dihydropyran, benzyl halides, alkyl halides, haloacetic acid, haloacetic acid esters, chlorocarbonic acid esters, alkylsulfonyl halides, aromatic sulfonyl halides, dialkyl dicarbonate or trialkylsilyl halides. Also suitable are polymers of p-(2-tetrahydropyranyl)-oxystyrene or p-(tert-butyloxycarbonyl)-oxystyrene with (meth)acrylic acid, (meth)acrylic acid esters and/or p-acetoxystyrene and polymers of p-hydroxystyrene and/or p-(2-tetrahydropyranyl)-oxystyrene with 3-hydroxybenzyl(meth)acrylates, which can, if necessary, additionally be protected by reaction with one of the compounds listed above.

Especially suitable are polymers that are—depending on the light sources used for irradiation—transparent in the wavelength range used for irradiation. Wavelengths can vary between 180 and 1500 nm. The polymers can carry both, groups that, after acid-catalysed deprotecting, bring about a change in solubility, and hydrophobic and hydrophilic groups that increase the solubility of the acid generator and ensure aqueous-alkaline developability. Examples of such polymers are acrylates and methacrylates prepared by co-, ter-, or quater-polymerisation from the corresponding monomers like methyl(meth)acrylate, (meth)acrylic acid, tert-butyl(meth)acrylate, 3-oxocyclohexyl(meth)acrylate, tetrahydropyranyl(meth)acrylate, adamantyl(meth)acrylate, cyclohexyl(meth)acrylate, norbornyl(meth)acrylate. The monomers can also combine two of above mentioned structures like for example (2-tetrahydropyranyl) oxynorbonylalcohol acrylates or (2-tetrahydropyranyl) oxymethyltricyclododecanemethanol methacrylates. Examples for such monomers are given in U.S. Pat. No. 5,621,019. The monomers may also carry organosilicon radicals in order, for example, to further increase the resistance in the case of dry etching processes, like for example trimethylsilylmethyl(meth)acrylate.

The invention accordingly also relates to a chemically amplified positive resist comprising as photosensitive acid donor a compound of formula I, II or III.

The invention relates also to a photoresist comprising polymers that are transparent down to the wavelength region of 180 nm.

A special embodiment of the positive resist according to the invention comprises from 75 to 99.5 percent by weight of a film-forming polymer that contains protecting groups (at the concentration from 1 to 60 mol percent, preferably from 5 to 50 mol percent against the amount of hydroxyl groups in the polymer) that can be removed by acid catalysis, and from 0.5 to 25 percent by weight of oximesulfonates of formula I, II or III, the percentages being based on the solids content of the compositions. In this context, preference is given to compositions comprising from 80 to 99 percent by weight of the mentioned polymer and from 1 to 20 percent by weight of oximesulfonate.

Another embodiment is a positive resist comprising from 40 to 90 percent by weight of an acid-inert film-forming polymer as binder, from 5 to 40 percent by weight of a monomeric or polymeric compound having protecting groups removable by acid catalysis and from 0.5 to 25 percent by weight of oximesulfonates of formula I, II or III, the percentages relating to the solids content of the compositions. Of those compositions, preference is given to those comprising from 50 to 85 percent by weight acid-inert binder, from 10 to 30 percent by weight monomeric or polymeric solution inhibitor and from 1 to 20 percent by weight, e.g. from 1 to 15 percent by weight, oximesulfonates.

Oximesulfonates can also be used as solubility enhancers, which can be activated by light. In that case, the compounds are added to a film-forming material comprising substantially no components that polymerise with the oximesulfonic acid ester when heated or when irradiated with actinic radiation. However, the oximesulfonates reduce the speed at which the film forming material dissolves in a suitable developer medium. That inhibiting effect can be cancelled by irradiating the mixture with actinic radiation, so that a positive image can be produced. Such an application is described, for example, in EP 241423.

A further special embodiment of the invention is, finally, a positive resist comprising a compound of formula I, II or III and a binder that is virtually insoluble in an alkaline developer and that becomes soluble in the developer in the presence of the photolysis products of the compound of formula I, II or III. In this case the amount of the mentioned oximesulfonate compound is generally from 5 to 50 percent by weight, based on the solids content of the composition.

The use of the oximesulfonates according to the invention in chemically amplified systems, which operates on the principle of the removal of a protecting group from a polymer, generally produces a positive resist. Positive resists are preferred to negative resists in many applications, especially because of their greater resolution. There is, however, also interest in producing a negative image using the positive resist mechanism, in order to combine the advantages of the high degree of resolution of the positive resist with the properties of the negative resist. That can be achieved by introducing a so-called image-reversal step as described, for example, in EP 361906. For that purpose, the image-wise irradiated resist material is treated, before the developing step, with, for example, a gaseous base, the acid that has been produced image-wise being neutralised. Then, a second irradiation, over its whole area, and thermal aftertreatment are carried out and the negative image is then developed in the customary manner.

In addition to the mentioned constituents, both the negative and the positive photoresist compositions may additionally comprise one or more of the additives customarily used in photoresists in the amounts familiar to a person skilled in the art, for example flow improvers, wetting agents, adhesives, thixotropic agents, colourants, pigments, fillers, solubility accelerators and so on. The reaction can be accelerated by the addition of photosensitisers which shift and/or broaden the spectral sensitivity. These are especially aromatic carbonyl compounds, such as benzophenone, thioxanthone, anthraquinone and 3-acylcoumarin derivatives and also 3-(aroylmethylene)thiazolines, but also eosine, rhodanine and erythrosine colourants.

Other compounds that accelerate the acid formation or enhance the acid concentration may also be used in combination with the oximesulfonates of the formulae I; II or III according to the invention in positive or negative resists or imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

For application, the compositions must generally also comprise a solvent. Examples of suitable solvents are ethyl acetate, 3-methoxymethyl propionate, ethyl pyruvate, 2-heptanone, diethyl glycol dimethyl ether, cyclopentanone, cyclohexanone, γ-butyrolactone, ethyl methyl ketone, 2-ethoxyethanol, 2-ethoxyethyl acetate and especially 1-methoxy-2-propyl acetate. The solvent may also be in the form a mixture, for example of two or more of the above-mentioned solvents. The choice of solvent and the concentration depend, for example, on the nature of the composition and on the coating method.

The solution is uniformly applied to a substrate by means of known coating methods, for example by spin-coating, immersion, knife coating, curtain pouring techniques, brush application, spraying and reverse roller coating. It is also possible to apply the photosensitive layer to a temporary, flexible support and then to coat the final substrate by coating transfer (laminating).

The amount applied (coating thickness) and the nature of the substrate (coating substrate) are dependent on the desired field of application. The range of coating thicknesses can in principle include values from approximately 0.01 μm to more than 100 μm.

Possible areas of use of the composition according to the invention are as follows: use as photoresists for electronics, such as etching resists, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques. The coating substrates and processing conditions vary accordingly.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

After the coating operation, the solvent is generally removed by heating, resulting in a layer of the photoresist on the substrate. The drying temperature must of course be lower than the temperature at which certain components of the resist might be thermally cured. Care must be taken in that respect especially in the case of negative photoresists. In general, drying temperatures should not exceed from 80 to 130° C.

The resist coating is then irradiated image-wise. The expression "image-wise irradiation" includes irradiation in a predetermined pattern using actinic radiation, i.e. both irradiation through a mask containing a predetermined pattern, for example a transparency, and irradiation using a laser beam that is moved over the surface of the coated substrate, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997, 107 p 275–281 and by K. P. Nicolay in Offset Printing 1997, 6, p 34–37.

After the irradiation and, if necessary, thermal treatment, the unirradiated sites (in the case of positive resists) or the irradiated sites (in the case of negative resists) of the composition are removed in a manner known per se using a developer.

It is generally necessary to allow a certain period of time prior to the developing step in order to allow the acid-sensitive components of the resist composition to react. In order to accelerate that reaction and hence the development of a sufficient difference in solubility between the irradiated and unirradiated sections of the resist coating in the developer, the coating is preferably heated before being developed. The heating can also be carried out or begun during the irradiation. Temperatures of from 60 to 150° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under those processing conditions.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may be used, for example, for the developing. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5N, but are usually diluted in suitable manner before use. For example solutions having a normality of approximately 0.1 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of those solvents. A typical aqueous/organic developer system is based on Butylcellosolve®/water.

It is known from EP 592139 that oximesulfonates can be used as acid generators, which can be activated by light in compositions that are suitable for the surface treatment and cleaning of glass, aluminium and steel surfaces. The use of those compounds in such organosilane systems results in compositions that have significantly better storage stability than those obtained when the free acid is used.

Oximesulfonates can also be used to produce so-called print-out" images when the compound is used together with a colourant that changes colour when the pH changes, as described e.g. in Japanese Patent Application JP 4 328552-A or in U.S. Pat. No. 5,237,059. Such colourchange systems can be used according to EP 199672 also to monitor goods that are sensitive to heat or radiation. In addition the newly claimed compounds of formula I, II or III exhibit already a colour change on their own when they are exposed to light of suitable wavelength. This color-change must not be as pronounced as in the case of using it in combination with the beforementioned acid-sensitive colourants, but it is well visible.

In addition to a colour change, it is possible during the acid-catalysed deprotection of soluble pigment molecules (as described e.g. in EP 648770, EP 648817 and EP 742255) for the pigment crystals to be precipitated; this can be used in the production of colour filters as described e.g. in EP 654711 or print out images and indicator applications, when the colour of the latent pigment precursor differs from that of the precipitated pigment crystal.

Compositions using pH sensitive dyes or latent pigments in combination with oximesulfonates can be used as light indicators or simple throw away dosimeters. Especially for light, that is invisible to the human eye, like UV- or IR-light, such dosimeters are of interest.

The oximesulfonates of the present invention can also be used to shape polymers that undergo an acid induced transition into a state where they have the required properties using photolithography. For instance the oximesulfonates can be used to pattern conjugated emissive polymers as described in M. L. Renak; C. Bazan; D. Roitman; Advanced materials 1997, 9, 392. Such patterend emissive polymers can be used to manufacture microscalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coating, insulating layers and buffer layers in the production of microchips and printed circuit boards.

The formulations may also be used as conformal coatings, photoimagable dielectricas as they are used in sequential build up systems for printed cricuit boards, stress buffer layers and isolation layers in the manufacturing of computer chips.

It is known that conjugated polymers like, e.g. polyanilines can be converted from semiconductive to conductive state by means of proton doping. The oxime-sulfonates of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

Suitable for the crosslinking of compositions comprising compounds of formula I, II or III are radiation sources that emit radiation of a wavelength of approximately from 150 to 1500, for example from 180 to 1000 or preferably from 240 to 700 nanometers. Both point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the lamp and the substrate according to the invention to be irradiated can vary, for example, from 2 cm to 150 cm, according to the intended use and the type and/or strength of the lamp. Suitable light sources are therefore especially mercury vapour lamps, especially medium and high pressure mercury lamps, from the radiation of which emission lines at other wavelengths can, if desired, be filtered out. That is especially the case for relatively short wavelength radiation. The distance between the lamp and the workpiece can vary, for example, from 2 cm to 150 cm, according to the intended use and the type and/or strength of the lamp. It is, however, also possible to use low energy lamps (for example fluorescent tubes) that are capable of emitting in the appropriate wavelength range. An example thereof is the Philips TL03 lamp. Another type of light source that can be used are the light emitting diodes (LED) that emit at different wavelength throughout the whole spectrum either as small band emitting source or as broad band (white light) source. Also suitable are laser light sources, for example excimer lasers, such as Kr—F lasers for irradiation at 248 nm or Ar—F lasers at 193 nm. Lasers in the visible range and in the infrared range can also be used. Very especially suitable is radiation of the mercury h and g lines at wavelengths of 436 and 405 nanometers. A suitable laser-beam source is, for example, the argon-ion laser, which emits radiation at wavelengths of 454, 458, 466, 472, 478, 488 and 514 nanometers. Nd-YAG-lasers emitting light at 1064 nm and it's second and third harmonic (532 nm and 355 nm respectively) can also be used. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities. On irradiation, the oximesulfonate in the composition in the irradiated sections of the surface coating decomposes to form sulfonic acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are as well suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures.

The surface coating to be cured can be exposed directly to sunlight or daylight-equivalent light sources. The curing can, however, also take place behind a transparent layer (e.g. a pane of glass or a sheet of plastics).

The compounds of formulae I, II or III are generally added to the compositions in an amount from 0.1 to 30% by weight, for example from 0.5 to 10% by weight, especially from 1 to 5% by weight.

Subject of the invention is a method of crosslinking compounds that can be crosslinked under the action of an acid, which method comprises adding a compound of formula I, II and/or III to the above-mentioned compounds and irradiating imagewise or over the whole area with light having a wavelength of 180–1500 nm.

The invention relates also to the use of compounds of formulae I, II or III as photosensitive acid donors in the preparation of surface coatings, printing inks, printing plates, dental compositions, colour filters, resist materials or image-recording materials, or image-recording materials for recording holographic images, as well as to a method for the preparation of surface coatings, printing inks, printing plates, dental compositions, colour filters, resist materials and as image-recording material, or image-recording material for recording holographic images, which comprises irradiating a composition according to the invention with light having a wavelength of 180–1500 nm.

The invention further pertains to the use of a composition as described above for the preparation of surface coatings, printing inks, printing plates, dental compositions, colour filters, resist materials and as image-recording material, or image-recording material for recording holographic images as well as to a method for the preparation of surface coatings, printing inks, printing plates, dental compositions, colour filters, resist materials and as image-recording material, or image-recording material for recording holographic images, which comprises irradiating a composition as described above with light having a wavelength in the range of 180–1500 nm.

The examples which follow illustrate the invention in more detail. Parts and percentages, as in the remainder of the description and in the claims, are by weight unless indicated otherwise.

EXAMPLE 1

2-Methylsulfonyloxyimino-4-phenyl-but-3-enenitrile 3.44 g (0.02 mol) of 2-hydroxyimino-4-phenyl-but-3-enenitrile, (mp 127–129° C., prepared from cinnamaldoxime according to C. Trione et al, *J. Org. Chem.* 1993, 58, 2075) are dissolved in 20 ml of anhydrous tetrahydrofuran and cooled to 0° C. Methanesulfonyl chloride (1.7 ml, 0.022 mol) is added at once, followed by triethylamine (4.2 ml, 0.03 mol) dropwise over 15 min, keeping the temperature of the mixture at 5° C. The mixture is then stirred at 25° C. for two hours, and poured into 150 ml of iced water. The off-white precipitate is washed with ether, dried and recrystallyzed from 70 ml of ethanol, yielding 2.74 g (55%) of 2-methylsulfonyloxyimino-4-phenyl-but-3-enenitrile as colorless crystals, mp. 144–148° C. No attempt is made to recover more material from the ether extract.

| Elemental analysis: $C_{11}H_{10}N_2O_3S$ (250.28) | | | |
|---|---|---|---|
| | C [%] | H [%] | N [%] |
| calculated: | 52.79 | 4.03 | 11.19 |
| found: | 52.85 | 4.42 | 11.28 |

EXAMPLE 2

2-Methylsulfonyloxyimino-4-p-tolyl-but-3-enenitrile

2.1: 4-p-tolyl-but-3-enenitrile 6.17 g (0.03 mol) of 4-methyl-benzenediazonium tetrafluoroborate (mp 105–110° C.; prepared by nitrosation of p-toluidine with sodium nitrite in aqueous fluoboric acid according to A. Roe, Org. Reactions vol V, 1949,193) are suspended in 60 ml of ethanol. Allyl cyanide (4.0 g; 0.06 mol) and palladium acetate (67 mg; 0.3 mmol) are added, and the light orange suspension is heated gently to 46° C., at which temperature a gentle evolution of nitrogen is visible. The mixture is stirred at the same temperature until the nitrogen evolution ceases (ca 3 h), resulting in a dark brown clear solution. The reaction mixture is poured into 300 ml of cold water and extracted with 2×100 ml of hexane:ethyl acetate 85:15 (v:v). The organic phases are washed with saturated aqueous sodium bicarbonate, water, brine, and dried over magnesium sulfate. The light green solution is concentrated to ca 20 ml by rotary evaporation, and allowed to crystallize in the refrigerator. Filtration yields 2.5 g (53%) of 4-p-tolyl-but-3-enenitrile as very thin, colorless leaflets, mp 60–61° C., consisting of the pure (E) isomer, as determined by $^1$H-NMR.

2.2: 2-Hydroxyimino-4-p-tolyl-but-3-enenitrile

In a 3-necked 50 ml flask fitted with a sintered glass gas inlet tube, 2.13 g (0.0135 mol) of 4-p-tolyl-but-3-enenitrile are dissolved in 30 ml of methanol, and cooled to 0° C. Sodium hydroxide (0.54 g; 0.0135 mol) is added. The turbid, slightly brownish mixture is then treated with ca. 0.025 mol of gaseous methyl nitrite bubbled below the surface of the mixture through the gas inlet tube (methyl nitrite is generated by dropwise addition of [0.8 ml of $H_2SO_4$ conc+1.6 ml $H_2O$] to a suspension of sodium nitrite (1.72 g; 0.025 mol) in 3 ml of methanol:water 1:1 (v:v); see M. Itoh et al. Org. Synth. Coll vol. VI, 1988, 199). The mixture is then stirred overnight, allowing the temperature to rise to 25° C. The solvent is evaporated in vacuo, the residue is redissolved in water and extracted with toluene. The aqueous phase is then acidified with conc. HCl to pH ca 2, the beige precipitate is filtered, rinsed neutral with water, and dried under vacuum. The crude product is redissolved in ethyl acetate, filtered through a short pad of $SiO_2$, and evaporated. 2-Hydroxyimino-4-p-tolyl-but-3-enenitrile (1.9 g; 76%), mp 135–137° C. is obtained and used without further purification.

2.3: 2-Methanesulfonyloxyimino-4-p-tolyl-but-3-enenitrile

2-Hydroxyimino-4-p-tolyl-but-3-enenitrile (1.9 g; 0.01 mol) is dissolved in 15 ml of anhydrous tetrahydrofuran, and cooled to 0° C. Methanesulfonyl chloride (0.93 ml, 0.012 mol) is added at once, followed by triethylamine (2.1 ml, 0.015 mol) dropwise over 20 min, keeping the temperature of the mixture below 5° C. The mixture is then stirred at 5–10° C. for 3.5 hours, and poured into 200 ml of iced water. The suspension is extracted with ethyl acetate, the organic extract is washed neutral with water, then with brine, and dried over magnesium sulfate. Rotary evaporation of the solvent and recrystallization from 50 ml of ethanol yields 2-methanesulfonyloxyimino-4-p-tolyl-but-3-enenitrile (1.7 g; 64%) as off-white crystals, mp 134–135° C. with one part melting at 145° C. $^1$H-NMR reveals the presence of two isomers (probably E/Z around the imino double bond).

| Elemental analysis: $C_{12}H_{12}N_2O_3S$ (264.30) | | | |
|---|---|---|---|
| | C [%] | H [%] | N [%] |
| calculated: | 54.53 | 4.58 | 10.60 |
| found: | 54.58 | 4.76 | 10.72 |

EXAMPLE 3

2-Methylsulfonyloxyimino-4-(4-methoxy-phenyl)-but-3-enenitrile

3.1: Benzoic acid 1-cyano-3-(4-methoxy-phenyl)-allyl ester

Acetonitrile (25 ml) is added to a solution of potassium carbonate (3.45 g; 0.025 mol) in 15 ml of water and the mixture is cooled to 0° C. 4-Methoxycinnamaldehyde (8.1 g; 0.05 mol) dissolved in acetonitrile (25 ml) is added dropwise under efficient stirring over 30 min, keeping the temperature between 0 and 2° C., and the yellow mixture is further stirred 2 h at the same temperature. The phases are separated, the organic layer is washed with brine, dried over magnesium sulfate, and evaporated. The crude benzoic acid 1-cyano-3-(4-methoxyphenyl)-allyl ester (15 g), obtained as a pale yellow oil, is used for the next step without further purification.

3.2: 4-(4-Methoxy-phenyl)-but-3-enenitrile

Benzoic acid 1-cyano-3-(4-methoxy-phenyl)-allyl ester (15 g; ca 0.050 mol) is dissolved in 100 ml of anhydrous tetrahydrofuran. Tetrakis(triphenylphosphine)palladium (0.88 g; 0.8 mmol) and 4.8 ml of poly(methylhydrosiloxane) (ca 80 meq; Aldrich) are added, and the mixture is stirred at ca 20° C., cooling with a cold water bath. After 3 h 30 min, the mixture is concentrated by rotary evaporation, stirred with 150 ml of water to hydrolyze the siloxane. The polymer and organic materials are redissolved in $CH_2Cl_2$ and washed with saturated sodium bicarbonate to remove benzoic acid. Evaporation of the solvent and flash chromatography (150 g $SiO_2$; hexane:ethyl acetate 80:20 v:v) affords 4.9 g (57%) of pure 4-(4-methoxy-phenyl)-but-3-enenitrile, mp 75–76° C.

3.3: 2-Hydroxyimino-4-(4-methoxy-phenyl)-but-3-enenitrile 4-(4-Methoxy-phenyl)-but-3-enenitrile (5.0 g; 0.025 mmol) dissolved in 90 ml of methanol is treated with ca 0.050 mol of gaseous methyl nitrite in the same way as described in example 2.2. After stirring overnight at ca 25° C., the reaction mixture is rotary evaporated and partitioned between 200 ml of 0.5 N HCl and 200 ml ethyl acetate. The aqueous phase is extracted with 50 ml of ethyl acetate. The combined organic extracts are evaporated and purified by flash chromatography (150 g $SiO_2$; hexane:ethyl acetate 80:20 v:v); to yield 2-hydroxyimino-4-(4-methoxy-phenyl)-but-3-enenitrile 1.8 g (36%) as a yellow solid which is used for the next reaction without further purification.

3.4: 2-Methylsulfonyloxyimino-4-(4-methoxy-phenyl)-but-3-enenitrile 2-hydroxyimino-4-(4-methoxy-phenyl)-but-3-enenitrile (1.8 g; 9 mmol) is dissolved in 15 ml of anhydrous tetrahydrofuran, and cooled to 0° C. Methanesulfonyl chloride (0.93 ml, 0.012 mol) is added at once, followed by triethylamine (2 ml, 0.015 mol) dropwise over 20 min, keeping the temperature of the mixture below 5° C. The mixture is then stirred at 2° C. for 1 h 15 min, and poured into 200 ml of iced water. The suspension is extracted with ethyl acetate, the organic extract is washed neutral with water, then with brine, and dried over magnesium sulfate. Rotary evaporation of the solvent and recrystallization from 80 ml of ethanol yields 2-methylsulfonyloxyimino-4-(4-methoxy-phenyl)-but-3-enenitrile (1.02 g; 41%) as light yellow hair-like crystals, mp 147–152° C. (dec). $^1$H-NMR reveals the presence of only one isomer.

| Elemental analysis: $C_{12}H_{12}N_2O_4S$ (280.30) | | | |
|---|---|---|---|
|  | C [%] | H [%] | N [%] |
| calculated: | 51.42 | 4.32 | 9.99 |
| found: | 51.81 | 4.51 | 9.90 |

EXAMPLE 4

2-Methylsulfonyloxyimino-3-methyl-4-phenyl-but-3-enenitrile 1.5 g (ca 8 mmol) of crude 2-hydroxyimino-3-methyl-4-phenyl-but-3-enenitrile (prepared according to C. Trione et al, *J. Org. Chem.* 1993, 58, 2075 from α-methylcinnamaldoxime and obtained as a brown oil) is treated with methanesulfonyl chloride and triethylamine as described in example 3.4. The crude product is a brown oil which crystallizes upon trituration with hexane:ethyl acetate 80:20 (v:v). Recrystallization from 20 ml ethanol affords 2-methylsulfonyloxyimino-3-methyl-4-phenyl-but-3-enenitrile (0.86 g; 41%) as light beige crystals, mp 105–107° C.

| Elemental analysis: $C_{12}H_{12}N_2O_3S$ (264.30) | | | |
|---|---|---|---|
|  | C [%] | H [%] | N [%] |
| calculated: | 54.53 | 4.58 | 10.60 |
| found: | 54.74 | 4.76 | 10.52 |

EXAMPLE 5

2-Methylsulfonyloxyimino-3-oxo-5-phenyl-pent-4-enenitrile

5.1: 2-Hydroxyimino-3-oxo-5-phenyl-pent-4-enenitrile

Cinnamoyl acetonitrile (5.1 g; 0.03 mol) is dissolved in 50 ml of acetic acid. 10 ml of $H_2O$ are added and the mixture is cooled to 3° C. in an ice/salt bath. Partial precipitation occurs, but the mixture remains well stirrable. Sodium nitrite (4.14 g; 0.06 mol) is added by portions over 10 min, keeping the temperature between 3 and 5° C. Complete solution is observed during addition, but precipitation occurs again towards the end. The mixture is then stirred at 0° C. for 1.5 h. The mixture is diluted with 100 ml of iced water with stirring, the light ochre precipitate is filtered, and washed with ca 100 ml of water. The humid cake is redissolved in ether (100 ml), washed with water, brine and dried over magnesium sulfate. Rotary evaporation and drying affords 2-hydroxyimino-3-oxo-5-phenyl-pent-4-enenitrile (4.7 g; 78%) as a dark yellow solid (mp 144–145° C. dec) which is used without further purification in the next reaction step.

5.2: 2-Methylsulfonyloxyimino-3-oxo-5-phenyl-pent-4-enenitrile

2-Hydroxyimino-3-oxo-5-phenyl-pent-4-enenitrile (4.0 g; 0.02 mol) is treated with methanesulfonyl chloride and triethylamine as described in example 3.4. The crude brown product is recrystallized from 40 ml of ethanol. 2-Methylsulfonyloxyimino-3-oxo-5-phenyl-pent-4-enenitrile (2.2 g; %) is obtained as a light ochre solid (mp 163–165° C.).

EXAMPLE 6

4-{4-[4-(3-Cyano-3-methanesulfonyloxyimino-propenyl)-benzyl]-phenyl}-2-methanesulfonyloxyimino-but-3-enenitrile in formula II, $R_1'$ = 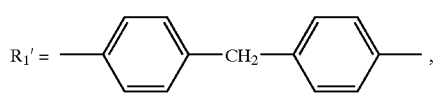, $R_2$=CN, $R_3$=—$SO_2CH_3$, $R_4$=$R_5$=H, m=0, n=1

6.1: 4,4'-Methanediyl-bis-benzenediazonium tetrafluoroborate 4,4'-Diaminodiphenylmethane (19.83 g; 0.10 mol) is dissolved in an aqueous solution of fluorboric acid (0.6 mol in 200 ml) at 0° C. Sodium nitrite (13.8 g; 0.20 mol) dissolved in 30 ml of water is then added dropwise at 4° C. during 1 h. A cream-colored precipitate is formed during the addition. After stirring for additional 1.5 h, the fine precipitate is filtered, washed with ice-cold 5% aqueous $HBF_4$ (40 ml), cold methanol (35 ml), and ether (120 ml). The crude product is dried in air overnight at room temperature, yielding 27.8 g (70%) of 4,4'-methanediyl-bis-benzenediazonium tetrafluoroborate as a tan solid, melting point 96–99° C. (dec).

6.2: 4-{4-[4-(3-Cyano-propenyl)-benzyl]-phenyl}-but-3-enenitrile

A suspension of 4,4'-methanediyl-bis-benzenediazonium tetrafluoroborate (11.9 g, 0.03 mol), prepared according to the method of example 6.1, allyl cyanide (8.05 g; 0.12 mol), and palladium acetate (0.135 g, 0.6 mmol) in 80 ml of ethanol is heated at 40° C. during 22 h. The heterogeneous reaction mixture is poured into 300 ml of water, extracted with ethyl acetate, washed with water, brine, dried over $MgSO_4$, and evaporated. The crude beige product is recrystallized from 130 ml of ethanol, yielding 5.44 g (61%) of 4-{4-[4-(3-cyano-propenyl)-benzyl]-phenyl}-but-3-enenitrile as light beige crystals, melting point 128–130° C.

6.3: 4-{4-[4-(3-Cyano-3-hydroxyimino-propenyl)-benzyl]-phenyl}-2-hydroxyimino-but-3-enenitrile A solution of sodium hydroxide (0.8 g; 0.02 mol) in 30 ml of methanol is added to a suspension of 4-{4-[4-(3-cyanopropenyl)-benzyl]-phenyl}-but-3-enenitrile (3.0 g; 0.01 mol), prepared as described in example 6.2, in 20 ml of methanol. Methyl nitrite, generated from 2.07 g (0.03 mol) of sodium nitrite as described in example 2.2, is bubbled through the suspension at 2° C. for 25 min, and the mixture is then left at room temperature for 48 h. The solvent is then evaporated, the residue is dissolved in 200 ml of water, extracted with toluene (the extract is discarded), and acidified with conc. hydrochloric acid. The beige precipitate is taken up in ethyl acetate, washed neutral with water, dried (MgSO$_4$) and concentrated by evaporation. 2.7 g (76%) of 4-{4-[4-(3-cyano-3-hydroxyimino-propenyl)-benzyl]-phenyl}-2-hydroxyimino-but-3-enenitrile are obtained as a light brown solid, melting point 142–145° C. (dec).

6.4: 4-{4-[4-(3-Cyano-3-methanesulfonyloxyimino-propenyl)-benzyl]-phenyl}-2-methanesulfonyloxyimino-but-3-enenitrile 4-{4-[4-(3-Cyano-3-methanesulfonyloxyimino-propenyl)-benzyl]-phenyl}-2-methanesulfonyloxyimino-but-3-enenitrile (2.7 g; 7.6 mmol), prepared as described in example 6.3, is dissolved in 15 ml of anhydrous tetrahydrofuran, and cooled to 0° C. Methanesulfonyl chloride (1.30 ml; 16.8 mmol) is added at once, followed by dropwise addition of triethylamine (3.2 ml; 23 mmol) during 35 min, keeping the temperature between 2° C. and 6° C. The mixture is then stirred at room temperature for 5 h, poured into 300 ml of iced water, extracted with dichloromethane, washed with aq. sat. NaHCO$_3$, water, brine, and dried over MgSO$_4$. Rotary evaporation and recrystallization from toluene (40 ml) affords 0.65 g (17%) of 4-{4-[4-(3-cyano-3-methanesulfonyloxyimino-propenyl)-benzyl]-phenyl}-2-methanesultonyloxyimino-but-3-enenitrile, as a light brown solid, melting point 178–186° C. (dec). $^1$H NMR (CDCl$_3$), δ [ppm]: 7.5 (6H, m), 7.2 (4H, m), 6.96 (2H, d, J=16.2 Hz), 4.06 (2H, m, (Ar)$_2$CH$_2$), 3.27 (6H, m, CH$_3$S).

EXAMPLE 7

2-[4'-(1-Cyano-3-p-tolyl-allylideneaminooxysulfonyl)-biphenyl-4-ylsulfonyloxyimino]-4-p-tolyl-but-3-enenitrile in formula III, R$_1$=4-tolyl, R$_2$=CN,

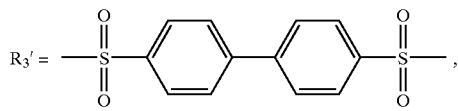

R$_4$=R$_5$=H, m=0, n=1

5.0 g (0.027 mol) of 2-hydroxyimino-4-p-tolyl-but-3-enenitrile (prepared as described in example 2.2) are dissolved in 15 ml of anhydrous tetrahydrofuran. Triethylamine (3.1 g; 0.03 mol) is added, and the solution is cooled to 5° C. Diphenyl-4,4'-disulfonyl chloride (4.29 g; 0.012 mol) dissolved in 35 ml of anhydrous THF is added dropwise over 90 min, keeping the temperature between 5 and 10° C. A thick, beige suspension forms, and 25 ml of THF are added to keep the mixture well stirrable. After 22 h at room temperature, the mixture is poured into water, the beige solid is filtered and washed neutral with water and dried i.v. at 40° C. The crude product is taken up in ethanol, filtered and dried i.v. at 40° C. The desired product, 2-[4'-(1-cyano-3-p-tolyl-allylideneaminooxysulfonyl)-biphenyl-4-ylsulfonyloxyimino]-4-p-tolyl-but-3-enenitrile, 7.7 g (90%) is obtained as a light beige solid, melting point >200° C.

| Elemental analysis: C$_{34}$H$_{26}$N$_4$O$_6$S$_2$ (650.74) | | | |
|---|---|---|---|
| | C [%] | H [%] | N [%] | S [%] |
| calculated: | 62.76 | 4.03 | 8.61 | 9.85 |
| found: | 62.90 | 4.02 | 8.53 | 9.90 |

EXAMPLE 7

Preparation of a Negative Resist

A resist solution is prepared by dissolving 65 parts of polyvinylphenol (Mw=4.000, Maruzen Chemicals Co. Ltd.), 30 parts of hexa(methoxymethyl)melamine ($^{RTM}$CYMEL 303, Cyanamid) and 5 parts of the latent acid to be tested in 7.5 g of 1-methoxy-2-propylacetate, which contains 1000 ppm of an anti-foaming agent (FC430). This solution is spin coated onto the polished side of a silicon wafer (diameter 4 inch), which has been pretreated with hexamethyldisilazane, by spinning at 6100 rpm for 30 seconds. The solvent is removed by drying the coated wafer for 60 seconds at 110° C. on a hot plate (pre-bake). Resulting are films of 1 μm thickness. Irradiation of the samples is performed with a Canon maskaligner (Canon PLA 501) using interference filters to select the wavelengths at 365, 405 and 436 nm. For each wavelength a fixed dose is used, but due to the lower output of the lamp and absorption of the latent acid, longer irradiation times respectively higher doses are used at longer wavelength in order to cause sufficient crosslinking. A special mask containing a greyscale step wedge (transmissions ranging from 0 to 50%) and resolution patterns is used. After exposure the wafers are heated for 60 seconds to 110° C. to perform the post exposure bake (PEB) during which the liberated acid catalyses the crosslinking reaction in the irradiated areas. Developing is performed by dipping the samples into a 2.38% solution of tetramethyl ammonium hydroxide (TMAH) for 60 seconds. The thickness of the film before exposure as well as after exposure in the fields that were exposed to different doses is measured with an Axiotron from Zeiss which uses white light interference. The thickness measurements are used to estimate the one-to-one energy E1:1 which is the dose that is required to retain the same film thickness as before developing. The film thickness of the cured samples is also measured by means of an Alpha Step profilometer. The step with the highest number that is cured is used to calculate the minimum dose E0 required to achieve crosslinking. The smaller the required dose the more reactive is the latent acid.

The results are listed in Table 1 and show that the latent acids have high sensitivity in a negative resist at all wavelengths.

TABLE 1

| Latent acid compound of example | Reactivity at 365 nm (mJ/cm$^2$) | Reactivity at 405 nm (mJ/cm$^2$) | Reactivity at 436 nm (mJ/cm$^2$) |
|---|---|---|---|
| 1 | E0 5 | — | — |
|   | E1:1 7 | | |
| 2 | E0 1.3 | E0 135 | — |
|   | E1:1 1.7 | E1:1 140 | |
| 3 | E0 0.7 | E0 2.3 | E0 37 |
|   | E1:1 1.6 | E1:1 5.5 | E1:1 49 |

TABLE 1-continued

| Latent acid compound of example | Reactivity at 365 nm (mJ/cm$^2$) | Reactivity at 405 nm (mJ/cm$^2$) | Reactivity at 436 nm (mJ/cm$^2$) |
|---|---|---|---|
| 4 | E0 7.2<br>E1:1 9.5 | — | — |

What is claimed is:

1. Compounds of formulae I, II or III

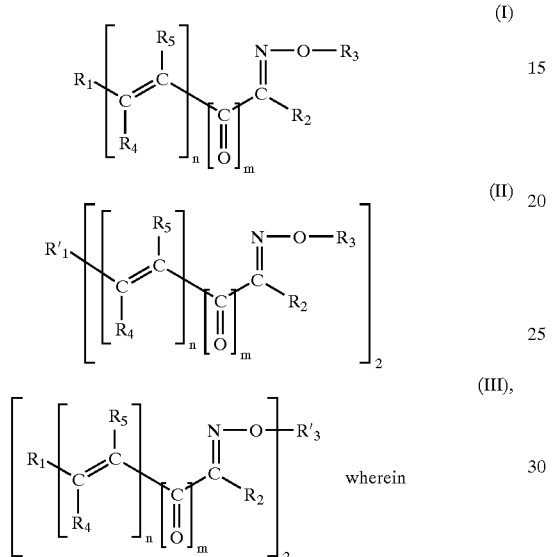

wherein m is zero or 1;

n is 1, 2 or 3;

$R_1$ is phenyl, which is unsubstituted or substituted by one or more of the radicals $C_1$–$C_{12}$alkyl, $C_1$–$C_4$haloalkyl, halogen, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$, with further substituents on the phenyl ring or with one of the carbon atoms of the phenyl ring; or $R_1$ is naphthyl, anthracyl or phenanthryl, wherein the radicals naphthyl, anthracyl and phenanthryl are unsubstituted or substituted by $C_1$–$C_6$alkyl, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$ with further substituents on the naphthyl, anthracyl or phenanthryl ring or with one of the carbon atoms of the naphthyl, anthracyl or phenanthryl ring;

or $R_1$ is a heteroaryl radical which is unsubstituted or substituted by $C_1$–$C_6$alkyl, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$ with further substituents on the heteroaryl ring or with one of the carbon atoms of the heteroaryl ring;

or $R_1$ is $C_2$–$C_{12}$alkenyl, $C_4$–$C_8$cycloalkenyl, or $C_6$–$C_{12}$bicycloalkenyl, with the proviso that the double bond (or the double bonds) of the radicals $C_2$–$C_{12}$alkenyl, $C_4$–$C_8$cycloalkenyl, or $C_6$–$C_{12}$bicycloalkenyl is (are) conjugated with the double bond substituted by $R_4$ and $R_5$; or, if m is zero, $R_1$ additionally is benzoyl, 2-furoyl, 2-thiophenecarbonyl, 2-pyridinecarbonyl or 2-pyrrolecarbonyl, wherein the radicals benzoyl, 2-furoyl, 2-thiophenecarbonyl, 2-pyridinecarbonyl or 2-pyrrolecarbonyl are unsubstituted or substituted by one or more of the radicals $C_1$–$C_{12}$alkyl, $C_1$–$C_4$haloalkyl, halogen, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$, with further substituents on the benzoyl, 2-furoyl, 2-thiophenecarbonyl, 2-pyridinecarbonyl or 2-pyrrolecarbonyl ring or with one of the carbon atoms of the benzoyl, 2-furoyl, 2-thiophenecarbonyl, 2-pyridinecarbonyl or 2-pyrrolecarbonyl ring; or, if m is zero, n is 1 and simultaneously $R_5$ is phenyl which is unsubstituted or substituted by one or more $C_1$–$C_{12}$alkyl, $C_1$–$C_4$haloalkyl, halogen, phenyl, $OR_6$, $NR_7R_8$, $SR_9$ and/or —S-phenyl, $R_1$ additionally is hydrogen or halogen;

$R'_1$ is vinylene, phenylene, naphthylene,

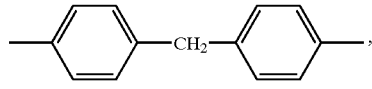

diphenylene or oxydiphenylene, wherein the radicals phenylene, naphthylene,

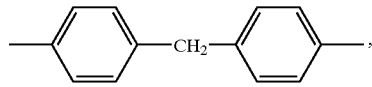

diphenylene and oxydiphenylene are unsubstituted or substituted by $C_1$–$C_{12}$alkyl;

$R_2$ is CN, $C_1$–$C_4$haloalkyl, $C_2$–$C_6$alkoxycarbonyl, phenoxycarbonyl, $C_1$–$C_6$alkyl-S(O)$_x$—, $C_6$–$C_{12}$aryl-S(O)x—, which is unsubstituted or substituted by $C_1$–$C_{12}$alkyl, or $R_2$ is $C_1$–$C_6$alkyl-SO$_2$O—, $C_6$–$C_{10}$aryl-SO$_2$O—, diphenyl-phosphinoyl or $R_2$ is benzoyl which is unsubstituted or substituted by CN, NO$_2$ or $C_1$–$C_4$haloalkyl;

x is 1 or 2;

$R_3$ is $C_1$–$C_{18}$alkylsulfonyl, phenyl-$C_1$–$C_3$alkylsulfonyl, camphorylsulfonyl, $C_1$–$C_{10}$haloalkylsulfonyl, phenylsulfonyl, naphthylsulfonyl, anthracylsulfonyl or phenanthrylsulfonyl, wherein the groups phenyl, naphthyl, anthracyl and phenanthryl of the radicals phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, NO$_2$, $C_1$–$C_{16}$alkyl, phenyl, $C_1$–$C_4$alkylthio, $OR_6$, COOR$_9$, $C_1$–$C_4$alkyl-OCO—, $R_9$OSO$_2$— and/or —NR$_7$R$_8$; or $R_3$ is $C_2$–$C_6$haloalkanoyl, halobenzoyl, triphenylsilyl, or a group

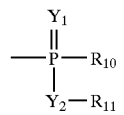

or

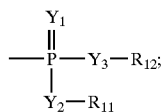

$Y_1$, $Y_2$ and $Y_3$ are independently of each other O or S;
$R'_3$ is $C_2$–$C_{12}$alkylenedisulfonyl, phenylenedisulfonyl, naphthylenedisulfonyl,

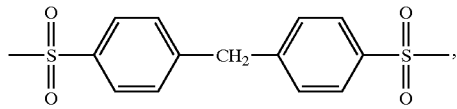

diphenylenedisulfonyl, or oxydiphenylenedisulfonyl, wherein the groups phenylene, naphthylene,

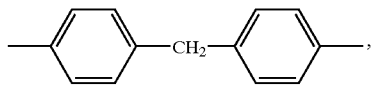

diphenylene and oxydiphenylene of the radicals phenylenedisulfonyl, naphthylenedisulfonyl,

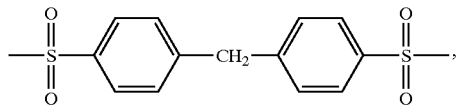

diphenylenedisulfonyl, or oxydiphenylenedisulfonyl are unsubstituted or substituted by $C_1$–$C_{12}$alkyl;

$R_4$ and $R_5$ are independently of each other hydrogen, halogen, $C_1$–$C_8$alkyl, $C_1$–$C_6$alkoxy, $C_1$–$C_4$haloalkyl, CN, $NO_2$, $C_2$–$C_6$alkanoyl, benzoyl, phenyl, —S-phenyl, $OR_6$, $SR_9$, $NR_7R_8$, $C_2$–$C_6$alkoxycarbonyl or phenoxycarbonyl, or $R_4$ and $R_5$ together are a direct bond;

$R_6$ is hydrogen, phenyl, $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl, or $R_6$ is $C_2$–$C_{12}$alkyl which is interrupted by one or more —O— or —S—, wherein the interrupted $C_2$–$C_{12}$alkyl is unsubtstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl;

$R_7$ and $R_8$ are independently of each other hydrogen or $C_1$–$C_{12}$alkyl which is unsubstituted or substituted by OH, $C_1$–$C_4$alkoxy, $C_1$–$C_{12}$alkylsulfonyl, phenylsulfonyl, (4-methyl-phenyl)sulfonyl and/or $C_1$–$C_6$alkanoyl; or $R_7$ and $R_8$ are $C_2$–$C_{12}$alkyl which is interrupted by one or more —O—, wherein the —O-interrupted $C_2$–$C_{12}$alkyl is unsubtstituted or substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or $R_7$ and $R_8$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl; or $R_7$ and $R_8$, together with the nitrogen atom to which they are bonded, form a 5-, 6- or 7-membered ring which may be interrupted by —O— or by —$NR_6$—;

$R_9$ is $C_1$–$C_{12}$ alkyl which is unsubstituted or substituted by OH and/or $C_1$–$C_4$alkoxy, or $R_9$ is $C_2$–$C_{12}$alkyl which is interrupted by one or more —O— or —S— and which interrupted $C_2$–$C_{12}$alkyl is unsubstituted or substituted by OH and/or $C_1$–$C_4$alkoxy;

$R_{10}$, $R_{11}$ and $R_{12}$ independently of one another are $C_1$–$C_6$alkyl which is unsubstituted or substituted by halogen; or $R_{10}$, $R_{11}$ and $R_{12}$ are phenyl which is unsubstituted or substituted by $C_1$–$C_4$alkyl or halogen; or $R_{11}$ and $R_{12}$ together are 1,2-phenylene or $C_2$–$C_6$alkylene which is unsubstituted or substituted by $C_1$–$C_4$alkyl or halogen;

with the proviso that if m and n both are 1, $R_4$ and $R_5$ both are hydrogen and $R_1$ is phenyl, $R_3$ is not p-tolylsulfonyl.

2. Compounds of formula I, according to claim 1, wherein
n is 1, m is zero or 1,
$R_1$ is unsubstituted phenyl or phenyl substituted by $C_1$–$C_4$alkyl or $OR_6$;
$R_2$ is CN;
$R_3$ is $C_1$–$C_4$alkylsulfonyl; and $R_4$ and $R_5$ independently of each other are hydrogen or $C_1$–$C_4$alkyl.

3. Compounds according to claim 1 having the structure Ia,

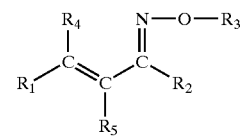

(Ia)

wherein
$R_1$, $R_2$, $R_3$, $R_4$ and $R_5$ are as defined in claim 1.

4. Compounds of formula Ia, according to claim 3, wherein
$R_1$ is unsubstituted phenyl or phenyl substituted once or twice by $C_1$–$C_4$alkyl, $OR_6$ or halogen or $R_1$ is cyclohexenyl, furyl or thienyl;
$R_2$ is CN or trifluoromethyl;
$R_3$ is $C_1$–$C_{16}$alkylsulfonyl; camphorylsulfonyl; or phenylsulfonyl which is unsubstituted or substituted 1–5 times by $C_1$–$C_{12}$alkyl, $C_1$–$C_4$alkoxy, $C_1$–$C_4$haloalkyl, $C_1$–$C_4$alkylthio, $NO_2$ or halogen; or $R_3$ is —P(O)($OR_{11}$)($OR_{12}$);
$R_4$ and $R_5$ independently of each other are hydrogen, $C_1$–$C_4$alkyl, phenyl, $C_1$–$C_4$alkoxy or $C_2$–$C_6$-alkoxycarbonyl;
$R_6$ is $C_1$–$C_4$alkyl or $C_1$–$C_4$alkylsulfonyl; and
$R_{11}$, $R_{12}$ are $C_1$–$C_6$alkyl or phenyl.

5. A composition comprising
a) at least one compound which can be crosslinked under the action of an acid and/or
b) at least one compound the solubility of which is altered under the action of an acid and
c) as latent acid photoinitiator, at least one compound of formulae I, II or III according to claim 1.

6. A composition according to claim 5, which comprises in addition to component c) further photoinitiators, sensitisers and/or additives.

7. A method for the preparation of surface coatings, printing inks, printing plates, dental compositions, colour filters, resist materials and as image-recording material, or image-recording material for recording holographic images, which comprises irradiating a composition according to claim 6 with light having a wavelength in the range of 180–1500 nm.

8. A method for the preparation of surface coatings, printing inks, printing pates, dental compositions, colour filters, resist materials and as image-recording material, or image-recording material or recording holographic images, which comprises irradiating a composition according to claim 5 with light having a wavelength in the range of 180–1500 nm.

9. A method of crosslinking compounds which can be crosslinked under the action of an acid, which method comprises adding a compound of formula I, II and/or III according to claim 1 to the above-mentioned compounds and irradiating imagewise or over the whole area with light having a wavelength in the range of 180–1500 nm.

10. A photoresist comprising as photosensitive acid donor at least one compound of formula I, II and/or III according to claim 1.

11. A photoresist according to claim 10, which photoresist is a negative resist.

12. A photoresist according to claim 10, which photoresist is a positive resist.

13. A photoresist according to claim 10, which photoresist is a chemically amplified resist.

14. A photoresist according to claim 10, comprising polymers that are transparent down to the wavelength region of 180 nm.

15. Compounds of formula I or II according to claim 1, wherein m is zero or 1;

n is 1;

$R_1$ is unsubstituted phenyl or phenyl which is substituted by $C_1$–$C_6$alkyl, phenyl, $OR_6$, $SR_9$, —S-phenyl, halogen and/or by $NR_7R_6$, it being possible for the substituents $OR_6$, and $NR_7R_8$ to form 5- or 6-membered rings, via the radicals $R_6$, $R_7$ and/or $R_8$ with further substituents of the phenyl ring, or with one of the carbon atoms of the phenyl ring; or $R_1$ is $C_4$–$C_8$cycloalkenyl or $C_6$–$C_{12}$bicycloalkenyl;

$R'_1$ is phenylene, naphthylene,

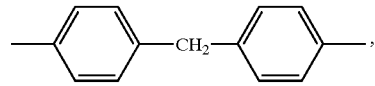

diphenylene or oxydiphenylene, wherein the radicals phenylene, naphthylene,

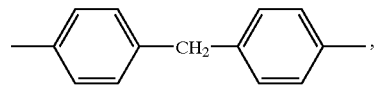

diphenylene and oxydiphenylene are unsubstituted or substituted by $C_1$–$C_{12}$alkyl.

* * * * *